(12) United States Patent
Esteghamatian et al.

(10) Patent No.: US 6,225,467 B1
(45) Date of Patent: *May 1, 2001

(54) ELECTROLUMINESCENT (EL) DEVICES

(75) Inventors: Mohammad Esteghamatian, Hamilton; Nan-Xing Hu, Oakville; Zoran D. Popovic, Mississauga; Ah-Mee Hor, Mississauga; Beng S. Ong, Mississauga, all of (CA)

(73) Assignee: Xerox Corporation, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/489,754

(22) Filed: Jan. 21, 2000

(51) Int. Cl.$^7$ .......................... C07D 251/24; H05B 33/14
(52) U.S. Cl. .......................... 544/180; 544/216; 428/690
(58) Field of Search .................................... 544/216, 180; 428/690

(56) References Cited

U.S. PATENT DOCUMENTS

| 3,172,862 | 3/1965 | Gurnee et al. | 252/301.3 |
|---|---|---|---|
| 3,530,325 | 9/1970 | Mehl et al. | 313/108 |
| 4,356,429 | 10/1982 | Tang | 313/503 |
| 4,539,507 | 9/1985 | VanSlyke et al. | 313/504 |
| 4,720,432 | 1/1988 | VanSlyke et al. | 428/457 |
| 4,769,292 | 9/1988 | Tang et al. | 428/690 |
| 4,885,211 | 12/1989 | Tang et al. | 428/457 |
| 5,150,006 | 9/1992 | VanSlyke | 313/504 |
| 5,151,629 | 9/1992 | VanSlyke | 313/504 |
| 5,429,884 | 7/1995 | Namiki et al. | 428/690 |
| 5,516,577 | 5/1996 | Matsuura et al. | 428/212 |
| 5,891,587 | 4/1999 | Hu et al. | 428/690 |
| 5,925,472 | 7/1999 | Hu et al. | 428/690 |
| 5,932,363 | 8/1999 | Hu et al. | 428/690 |
| 5,942,340 | 8/1999 | Hu et al. | 428/690 |
| 5,952,115 | 9/1999 | Hu et al. | 428/690 |
| 6,057,048 | * 5/2000 | Hu et al. | 428/690 |

OTHER PUBLICATIONS

"Influence of the emission Site on the Running Durability of Organic Electroluminescent Devices", Hamada et al., *Jpn. J. Appl. Phys.*, vol. 34, (1995), pp. L824–L826.

"Aromatic Polyethers With 1,3,5–Triazine Units as Hole Blocking/Electron Transport Materials in ELDs", Fink et al., *Macromol. Symp.* 125, 151 to 155 (1997).

* cited by examiner

Primary Examiner—Richard L. Raymond
Assistant Examiner—Venkataraman Balasubramanian
(74) Attorney, Agent, or Firm—E. O. Palazzo

(57) ABSTRACT

The triazine

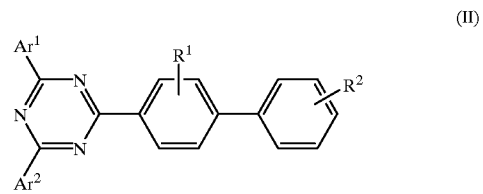

(II)

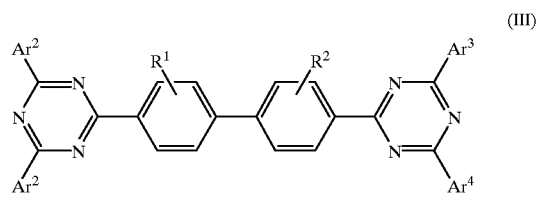

(III)

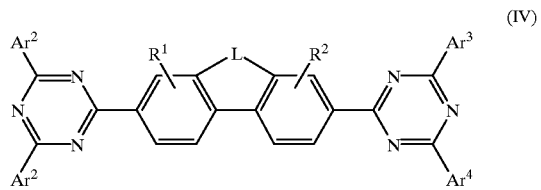

(IV)

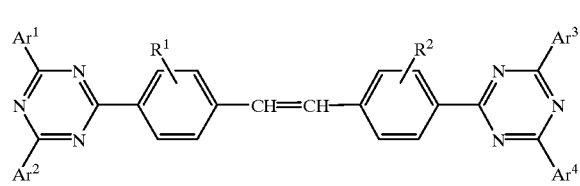

(V)

wherein $Ar^1$, $Ar^2$, $Ar^3$, and $Ar^4$ are each independently an aryl; $R^1$ and $R^2$ are substituents selected from the group consisting of hydrogen, an alkyl, an aryl, an alkoxy, a halogen atom, and a cyano; $R^3$ and $R^4$ are each a divalent group L selected from the group consisting of —C(R'R")—, alkylene, an oxygen atom, a sulfur atom, and —Si(R'R")—, wherein R' and R" are selected from the group consisting of hydrogen, alkyl, alkoxy, and aryl.

29 Claims, No Drawings

ELECTROLUMINESCENT (EL) DEVICES

PATENTS AND COPENDING APPLICATION

Illustrated in U.S. Pat. No. 5,942,340, U.S. Pat. No. 5,952,115, U.S. Pat. No. 5,932,363, U.S. Pat. No. 5,925,472, and U.S. Pat. No. 5,891,587, the disclosures of which are totally incorporated herein by reference, are EL devices. Illustrated in U.S. Ser. No. 09/164,753, the disclosure of which is totally incorporated herein by reference, is an electroluminescent device comprised of an anode, a hole transporting layer, a light emitting layer, and a cathode, wherein said light emitting layer contains a component of the formula

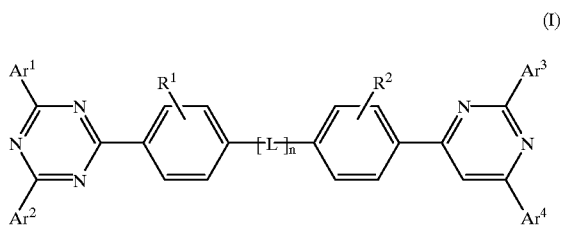

(I)

wherein $Ar^1$, $Ar^2$, $Ar^3$, and $Ar^4$ are each independently aryl or optionally aliphatic; $R^1$ and $R^2$ are independently selected from the group consisting of hydrogen, aliphatic, halogen, and cyano; L is a suitable linking group; and n is a number of from 0 to about 3. Illustrated in copending applications U.S. Ser. No. 09/489,527, and U.S. Ser. No. 09/489,144, the disclosures of which are totally incorporated herein by reference, are triazines and electroluminescent devices containing triazines. The appropriate components and processes of the above patents and copending applications may be selected for the present invention in embodiments thereof.

BACKGROUND OF THE INVENTION

This invention is generally directed to organic electroluminescent (EL) devices, and more specifically, to organic EL devices with a number of excellent desired performance characteristics, and which devices are desired that are capable of providing uniform luminescence, high electroluminescent efficiency, excellent durability, and low driving voltages. The organic EL devices of the present invention contain an electron transport component comprised of triazine compounds, and which devices can be selected for use in flat-panel emissive display technologies, including TV screens, computer screens, and the like.

PRIOR ART

A simple organic EL device can be comprised of a layer of an organic luminescent material conductively sandwiched between an anode, typically comprised of a transparent conductor, such as indium tin oxide, and a cathode, typically a low work function metal such as magnesium, calcium, aluminum, or the alloys thereof with other metals. The EL device functions on the principle that under an electric field, positive charges (holes) and negative charges (electrons) are respectively injected from the anode and cathode into the luminescent layer and undergo recombination to form excitonic states which subsequently emit light. A number of prior art organic EL devices have been prepared from a laminate of an organic luminescent material and electrodes of opposite polarity, which devices include a single crystal material, such as a single crystal anthracene, as the luminescent substance as described, for example, in U.S. Pat. No. 3,530, 325. However, these devices usually require excitation voltages on the order of 100 volts or greater.

An organic EL device with a multilayer structure can be formed as a dual layer structure comprising one organic layer adjacent to the anode supporting hole transport, and another organic layer adjacent to the cathode supporting electron transport and acting as the organic luminescent zone of the device. Another alternate device configuration is comprised of three separate layers, a hole transport layer, a luminescent layer, and an electron transport layer, which layers are laminated in sequence and are sandwiched between an anode and a cathode. Optionally, a fluorescent dopant material can be added to the emission zone or layer whereby the recombination of charges results in the excitation of the fluorescent.

In U.S. Pat. No. 4,539,507 there is disclosed an EL device formed of a conductive glass transparent anode, a hole transporting layer of 1,1-bis(4-p-tolylaminophenyl) cyclohexane, an electron transporting layer of 4,4'-bis(5,7-di-tert-pentyl-2-benzoxzolyl)stilben, and an indium cathode.

U.S. Pat. No. 4,720,432 discloses an organic EL device comprising a dual-layer hole injecting and transporting zone, one layer being comprised of porphyrinic compounds supporting hole injection and the other layer being comprised of aromatic tertiary amine compounds supporting hole transport.

U.S. Pat. No. 4,769,292 discloses an EL device employing a luminescent zone comprised of an organic host material capable of sustaining hole-electron recombination and a fluorescent dye material capable of emitting light in response to energy released by hole-electron recombination. A preferred disclosed host material is an aluminum complex of 8-hydroxyquinoline, namely tris(8-hydroxyquinolinate) aluminum.

Typically, the organic EL devices with multi-layered configurations comprise an electron transport layer in contact with a cathode. This electron transport layer is intended to assist injection of electrons from the cathode into the light-emitting layer. A variety of organic electron transport materials have been employed for this purpose. A class of such electron transport materials is comprised of the metal complexes of 8-hydroxyquinoline, as disclosed in U.S. Pat. No. 4,720,432. A another class of electron transport materials for EL devices is comprised of 1,3,5-oxidiazole compounds, such as those disclosed in *Japanese Journal of Applied Physics*, Part 2, vol. 34, L824 (1995). Also, certain 1,3,5-triazine containing materials have been reported as being a hole blocking layer in organic EL devices, see Fink et al. in *Macromolecular Symposia*, vol. 125, 151 (1997).

While recent progress in organic EL research has elevated the potential of organic EL devices for widespread applications, the performance levels of current available devices may still be below expectations. Further, for visual display applications, organic luminescent materials should provide a satisfactory color in the visible spectrum, normally with emission maxima at about 460, 550 and 630 nanometers for blue, green and red. The aforementioned metal complexes of 8-hydroxyquinoline, such as tris(8-hydroxyquinolinate)aluminum, generally fluoresce in green or longer wavelength region. These electron transport materials may be suitable for use in EL devices with light emission in green or longer wavelength region, however, for blue-emitting EL devices they are of limited use. Although prior art electron transport materials may fluoresce in the blue region, the performance characteristics of the resulting EL devices still possess many disadvantages such as poor operation stability. Thus, there continues to be a need for electron transport materials for organic EL devices, which are suitable for the design of EL devices with satisfactory emission in the visible spectrum of from blue to longer wavelength region. There is also a need for electron transport materials, which can improve EL device operation stability and durability, and a need for electron transport materials, which can enhance the EL charge transporting characteristics, thus lowering device driving voltages. Further, there is a need for electron transport materials for EL device comprised of a cathode comprised of a metal, such as aluminum, and which device can maintain desirable performance characteristics, such as low driving voltage, and excellent operation stability. Further, there is a need for electron transport materials, which are vacuum evaporable and form thin films with excellent thermal stability.

SUMMARY OF THE INVENTION

It is a feature of the present invention to provide improved organic EL devices with many advantages described herein.

It is another feature of the present invention to provide EL devices capable of providing satisfactory emission in the visible spectrum from blue to longer wavelength regions, for example from about 400 nanometers to about 700 nanometers, high electroluminescent efficiency, excellent durability, and low driving voltages, for example from about 10 to about 50 volts, and a luminence value of about 100 cd/m$^2$. In another feature of the present invention there are provided organic EL devices comprising an electron transport component comprised of specific triazine compounds, especially those containing biphenyl groups.

Further, in an feature of the present invention there are provided organic EL devices comprised of an anode and a cathode, and an organic luminescent medium containing an electron transport component comprised of triazine compounds, or comprised of a triazine electron acceptor and an amine electron donor connected by a polarizable linkage, such as an aromatic or aryl group.

In another feature of the present invention there are provided organic EL devices comprised of a supporting substrate of, for example, glass, an anode, a buffer layer, a hole transport layer, an electron transport layer, and in contact therewith a metal cathode, wherein the electron transport layer is comprised of an electron transport component comprised of specific novel triazine compounds.

Yet in another feature of the present invention there are provided organic EL devices comprised of a supporting substrate of, for example, glass, an anode, an optional buffer layer, a hole transport layer, a light emitting layer, an electron transport layer, and in contact therewith a metal cathode, wherein the electron transport layer is comprised of an electron transport component comprised of specific triazine compounds.

Specifically, it is a feature of the present invention to provide EL devices comprised of a supporting substrate of, for example, glass, an indium tin oxide anode, a buffer layer comprised of a tertiary aromatic amine optionally doped with an aromatic hydrocarbon such as rubrene, a vacuum deposited organic hole transporting layer comprised of, for example, 4,4'-bis(9-carbazolyl)-1,1'-biphenyl, a vacuum deposited electron transport layer comprised of specific triazine compounds, such as 4,4'-bis-[2-(4,6-diphenyl-1,3,5-triazinyl)]-1,1'-biphenyl, and in contact therewith a low work function metal, such as magnesium or aluminum, or their alloys.

Also, it is a feature of the present invention to provide EL devices comprised of a supporting substrate of, for example, glass, an indium tin oxide anode, an optional buffer layer, a vacuum deposited organic hole transporting layer comprised of, for example, N,N'-di-1-naphthyl-N,N'-diphenyl-1,1'-biphenyl4,4'-diamine optionally doped with an aromatic hydrocarbon such as rubrene, a vacuum deposited light-emitting layer comprised of, for example, tris(8-hydroxyquinolinate)aluminum, a vacuum deposited electron transport layer, a vacuum deposited electron transport layer comprised of specific triazine compounds such as 4,4'-bis-[2-(4,6-diphenyl-1,3,5-triazinyl)]-1,1'-biphenyl, and in contact therewith a low work function metal, such as magnesium or aluminum, or their alloys.

Aspects of the present invention relate to the triazine

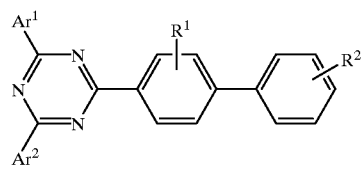

(II)

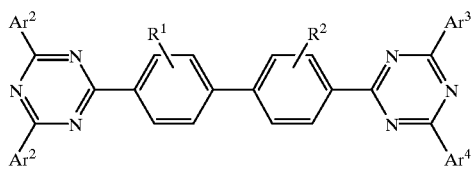

(III)

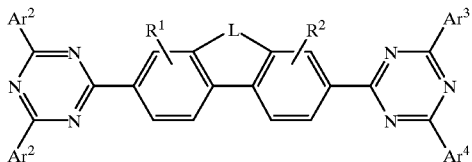

(IV)

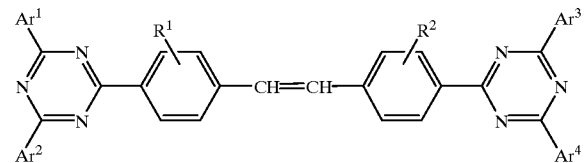

(V)

wherein Ar$^1$, Ar$^2$, Ar$^3$, and Ar$^4$ are each independently an aryl; R$^1$ and R$^2$ are substituents selected from the group consisting of hydrogen, an alkyl, an aryl, an alkoxy, a halogen atom, and a cyano; R$^3$ and R$^4$ are each a divalent group L selected from the group consisting of —C(R'R")—, alkylene, an oxygen atom, a sulfur atom, and —Si(R'R")—, wherein R' and R" are selected from the group consisting of hydrogen, alkyl, alkoxy, and aryl; a triazine wherein Ar$^1$, Ar$^2$, Ar$^3$, and Ar$^4$ are selected from the group consisting of a phenyl, a biphenylyl, a naphthyl, and a stilbenyl; and wherein the aryl group contains a substituent selected from the group consisting of hydrogen, an alkyl group with from 1 to about 6 carbon atoms, an alkoxy group with from 1 to about 6 carbon atoms, a halogen atom, and a cyano group; a triazine wherein the aryl is selected from the group consisting of a phenyl, a tolyl, a methoxyphenyl, a butylphenyl, a naphthyl, and a biphenylyl; and wherein R$^1$ and R$^2$ are hydrogen or methyl; a triazine wherein L is —C(R'R")—, wherein R' and R" is a hydrogen atom, an alkyl group containing from 1 to about 10 carbon atoms, or an alkoxyl group containing from 1 to about 10 carbon atoms; a triazine selected from the group consisting of 2,4,6-tris(4-biphenylyl)-1,3,5-triazine, 2,4,6-tris[4-(4'-methylbiphenylyl)]-1,3,5-triazine, 2,4,6-tris[4-(4'-tert-butylbiphenylyl)-1, 3,5-triazine, 2,4,6-tris[4-(4'-methoxybiphenylyl)]-1,3,5-triazine, 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3, 5-triazinyl)]-1,1'-biphenyl, 4,4'-bis-[2-(4,6-d i-m-methoxyphenyl-1,3,5-triazinyl)]-1,1'-biphenyl, 4,4'-bis-[2-(4-0-naphthyl-6-phenyl-1,3,5-triazinyl)]-1,1'-biphenyl, 2,7-bis-[2-(4,6-di-phenyl-1,3,5-triazinyl)]fluorene, 2,7-bis-[2-(4,6-di-phenyl-1,3,5-triazinyl)]-9,9-dimethylfluorene, 4,4'-bis-[2-(4,6-di-phenyl-1,3,5-triazinyl)]-stilbene, and 4,4'-bis-[2-(4-phenyl-6-m-tolyl-1,3, 5-triazinyl)]-stilbene; a triazine selected from the group consisting of 2,4,6-tris(4-biphenylyl)-1,3,5-triazine, 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-p-tert-butylphenyl-1,3,5-triazinyl)]-1,1'-biphenyl, and 4,4'-bis-[2-(4,6-di-phenyl-1,3, 5-triazinyl)]-stilbene; a triazine wherein $Ar^1$, $Ar^2$, $Ar^3$ and $Ar^4$ are phenyl; a triazine wherein $Ar^1$, $Ar^2$, $Ar^3$ and $Ar^4$ are naphthyl; a triazine wherein $Ar^1$, $Ar^2$, $Ar^3$ and $Ar^4$ are aryl with from about 6 to about 30 carbon atoms; a triazine wherein $R^1$ and $R^2$ are aryl; a triazine wherein $R^3$ and $R^4$ are alkylene with from about 2 to about 24 carbon atoms; a triazine wherein R' and R" are alkyl with about 1 to about 25 carbon atoms; a triazine wherein R' and R" are alkyl with about 1 to about 6 carbon atoms; a triazine wherein R' and R" are alkoxy with about 1 to about 25 carbon atoms; a triazine wherein R' and R" are alkoxy with about 1 to about 6 carbon atoms; a triazine wherein $R^3$ is oxygen; a triazine wherein $R^4$ is oxygen; a triazine of the formula

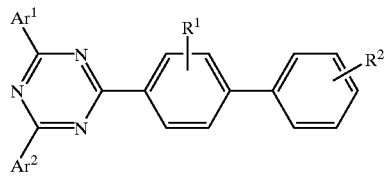

wherein $Ar^1$, and $Ar^2$ are each independently an aryl; and $R^1$ and $R^2$ are selected from the group consisting of hydrogen, an alkyl, an aryl, an alkoxy, a halogen atom, and a cyano; a triazine of the formula

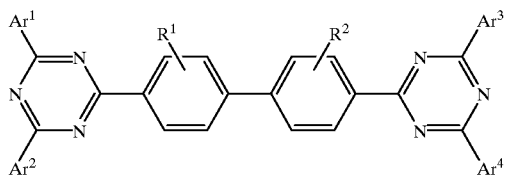

wherein $Ar^1$, $Ar^2$, $Ar^3$, and $Ar^4$ are each independently an aryl; R' and R² are selected from the group consisting of hydrogen, an alkyl, an aryl, an alkoxy, a halogen atom, and a cyano; a triazine of the formula

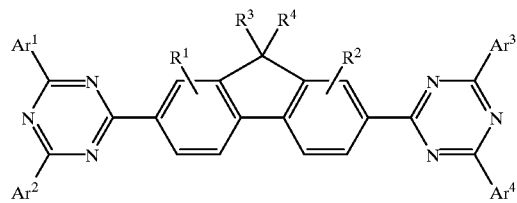

wherein $Ar^1$, $Ar^2$, $Ar^3$, and $Ar^4$ are each independently an aryl; $R^1$ and $R^2$ are selected from the group consisting of hydrogen, an alkyl, an aryl, an alkoxy, a halogen atom, and a cyano; $R^3$ and $R^4$ are each a divalent group L selected from the group consisting of (R'R")—, alkylene, an oxygen atom, a sulfur atom, and —Si(R'R")—, wherein R' and R" are selected from the group consisting of hydrogen, alkyl, alkoxy, and aryl; a triazine of the formula

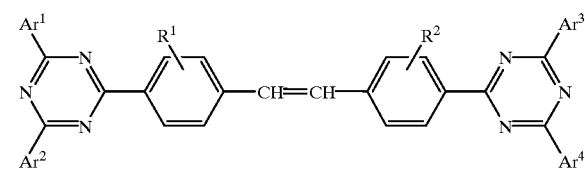

wherein $Ar^1$, $Ar^2$, $Ar^3$, and $Ar^4$ are each independently an aryl; $R^1$ and $R^2$ are selected from the group consisting of hydrogen, an alkyl, an aryl, an alkoxy, a halogen atom, and a cyano; an electroluminescent device containing as the electron transport a triazine illustrated herein; a triazine of the formulas (II)

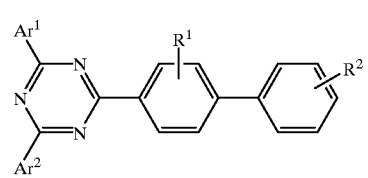

(III)

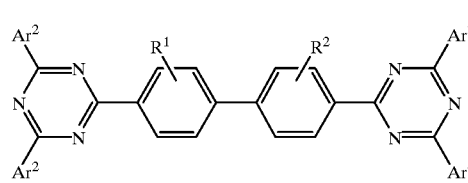

(IV)

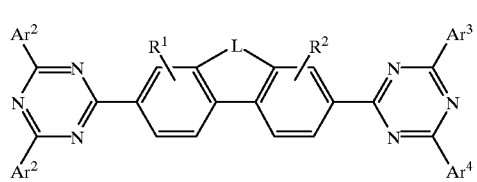

(V)

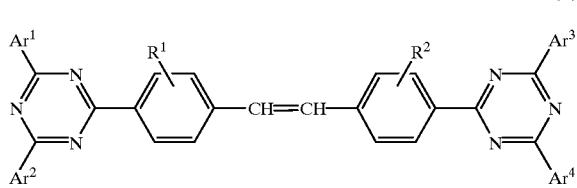

wherein $Ar^1$, $Ar^2$, $Ar^3$, and $Ar^4$ are each independently aromatic or aliphatic; $R^1$ and $R^2$ are selected from the group consisting of hydrogen, an alkyl, an aryl, an alkoxy, a halogen atom, and a cyano; $R^3$ and $R^4$ are each a divalent group L; a triazine wherein L is selected from the group consisting of —C(R'R")—, alkylene, an oxygen atom, a sulfur atom, and —Si(R'R")—, wherein R' and R" are selected from the group consisting of hydrogen, alkyl, alkoxy, and aryl, and $Ar^1$, $Ar^2$, $Ar^3$, and $Ar^4$ are aryl; a triazine wherein $Ar^1$, $Ar^2$, $Ar^3$, and $Ar^4$ are selected from the group consisting of a phenyl, a biphenylyl, a naphthyl, and a stilbenyl; and wherein the aryl group contains a substituent selected from the group consisting of hydrogen, an alkyl group with from 1 to about 6 carbon atoms, an alkoxy group with from 1 to about 6 carbon atoms, a halogen atom, and a cyano group; a triazine wherein alkyl contains from 1 to about 25 carbon atoms, and alkoxy contains from 1 to about 25 carbon atoms, and wherein the $R^1$ and $R^2$ are alkyl, or alkoxy, and electron transport electron injection, or mixtures thereof, components comprised of the triazine compounds illustrated by the formula

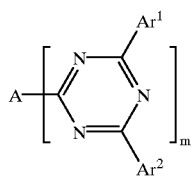

(I)

wherein $Ar^1$ and $Ar^2$ are independently aromatic, such as an aryl group, and which aryl can, for example, be selected from the group consisting of a phenyl, a stilbenyl, a biphenylyl, a naphthyl, a pyridyl, and a quinolyl and the like, and wherein the aryl group may further contain a substituent selected from the group consisting of hydrogen, an alkyl group with, for example, from 1 to about 10 carbon atoms, an alkoxy group with, for example, from 1 to about 10 carbon atoms, a dialkylamino group with preferably from about 1 to about 3 carbon atoms, a halogen, a cyano group and the like; m is a number of from 1 to about 4; and A is a monovalent or a multivalent aromatic group which contains at least two conjugate-linked or two fused aromatic rings, such as from about 2 to about 10.

Examples of monovalent or multivalent groups A are

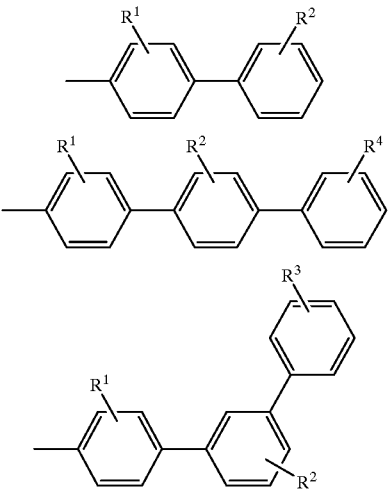

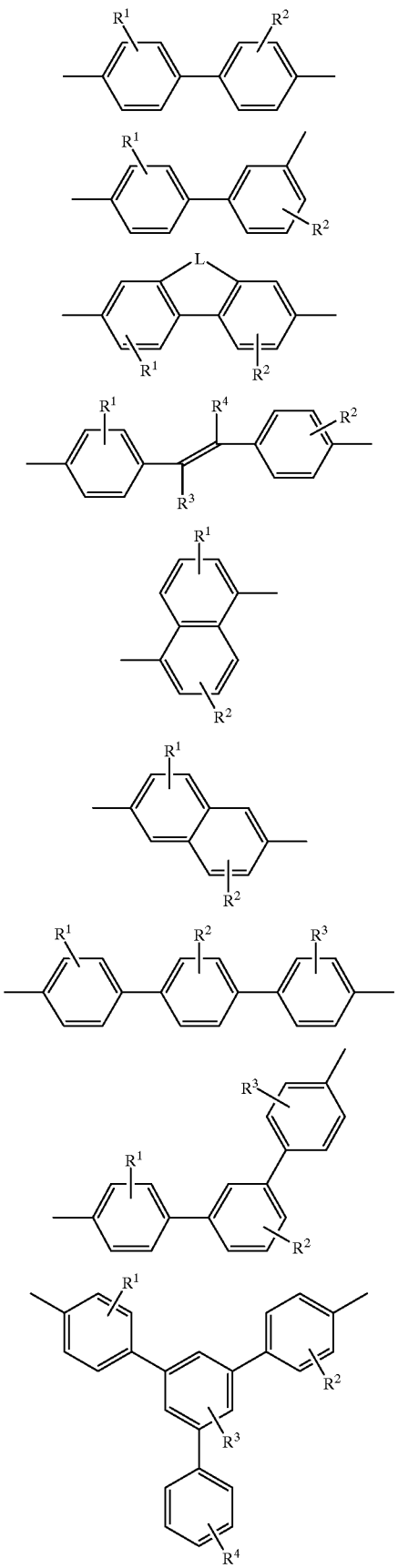

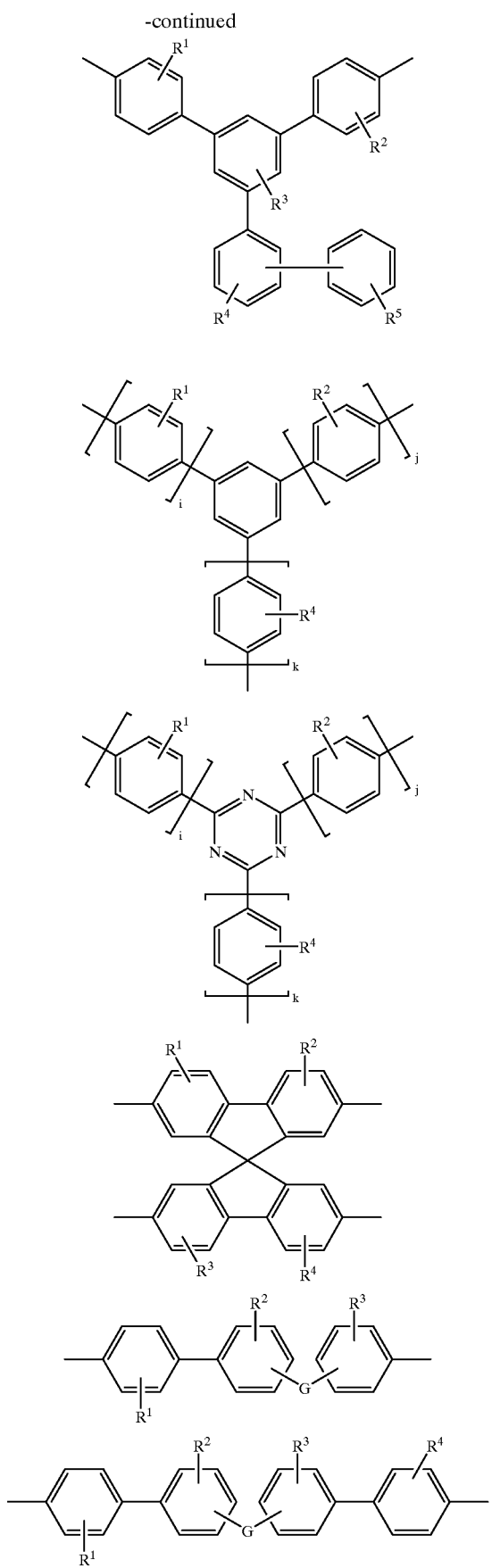

wherein $R^1$ to $R^5$ are each independently a substituent, preferably selected from the group consisting of hydrogen aliphatic, such as an alkyl group, an alkoxy group, a halogen such as a chloride atom, a cyano group, and the like; L is a divalent group which may be selected from the group consisting of —(R'R")—, an ethylene, —Si(R'R")—, an oxygen atom, a sulfur atom, and the like, wherein R' and R" is a hydrogen atom, an alkyl group containing from 1 to about 10 carbon atoms, or an alkoxyl group containing from 1 to about 10 carbon atoms, or an aryl; G is a divalent linkage, which may be selected from the group consisting of —C(R'R")—, an alkylene like ethylene, Si(R'R")—, an oxygen atom, a sulfur atom, and the like, preferably L is —C(R'R")—, wherein R' and R" is a hydrogen atom, an alkyl group containing from 1 to about 5 carbon atoms, or an aryl; and i, j, k are a number of from 1 to about 3.

A particularly preferred class of triazine components or compounds are illustrated by the following formula

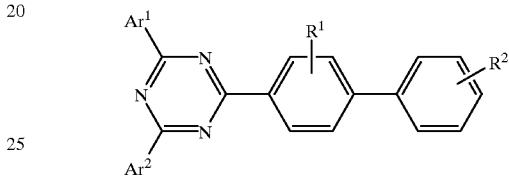

(II)

wherein $Ar^1$ and $Ar^2$ are each independently aryl, and aryl can be selected, for example, from the group consisting of a phenyl, a stilbenyl, a biphenyl, a naphthyl, a pyridyl, and a quinolyl and the like, and wherein the aryl group may further contain a suitable substituent selected, for example, from the group consisting of hydrogen, an alkyl group, an alkoxy group, a dialkylamino, a halogen, a cyano group and the like; $R^1$ and $R^2$ are, for example, substituents selected from the group consisting of hydrogen, aliphatic such as an alkyl group, and an alkoxy group; a halogen such as a chloride atom, a cyano group, and the like.

Another preferred class of triazine components or compounds are illustrated by the following formula

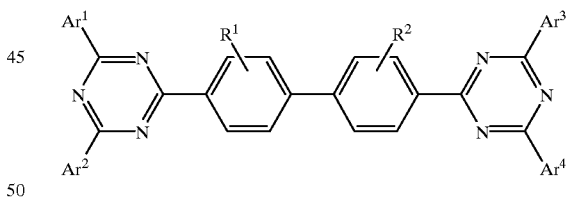

(III)

wherein $Ar^1$, $Ar^2$, $Ar^3$, and $Ar^4$; and the substituents of $R^1$ and $R^2$ are as indicated herein. The compounds of Formula (III) may further contain a linkage, and more specifically, be of the formula represented by

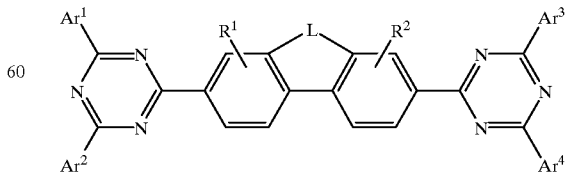

(IV)

wherein the aryl groups of $Ar^1$, $Ar^2$, $Ar^3$, and $Ar^4$, and the substituents of $R^1$ and $R^2$ are as indicated herein; L is a divalent group which may be selected from the group consisting of —C(R'R")—, an alkylene like ethylene, —Si(R'R")—, an oxygen atom, a sulfur atom, and the like, wherein R' and R" is a hydrogen atom, an alkyl group preferably containing from 1 to about 10 carbon atoms, or an alkoxyl group preferably containing from 1 to about 10 carbon atoms; or L is $R^3$ and $R^4$ as illustrated herein.

Yet another preferred class of triazine components or compounds are illustrated by the following formula (V)

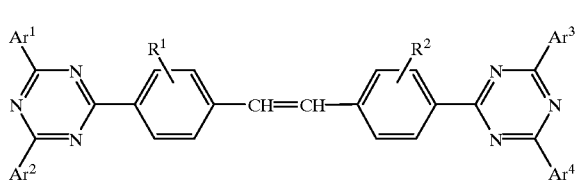

wherein the aryl groups of $Ar^1$, $Ar^2$, $Ar^3$, and $Ar^4$; and the substituents of $R^1$ and $R^2$ are as illustrated herein.

In embodiments, the present invention relates to organic EL devices that are comprised of a supporting substrate of, for example, glass, an anode, an organic luminescent medium or layer in contact with a cathode, wherein the organic luminescent layer contains an electron transport component comprised of the triazines illustrated herein. In a preferred embodiment, the organic luminescent medium is comprised of an optional buffer layer, an organic hole transport layer, and an electron transport layer comprised of the triazine compound illustrated herein, wherein either of the hole transport layer or the electron transport layer may serve as a light emitting layer. In another preferred embodiment, the organic luminescent medium is comprised of a buffer layer, an organic hole transport layer, a light-emitting layer, and an electron transport layer comprised of the triazine compounds illustrated herein, and wherein the light emitting layer may further contain a fluorescent material capable of emitting light in response to energy released by the hole-electron recombination.

The triazine compounds of the present invention which can readily be evaporated to deposit thin films with desirable morphological and thermal stability exhibit acceptable to excellent electron transport properties, and excellent chemical and electrical stability.

In embodiments, such as where the triazine compound preferably of formulas (II) to (V), are selected as an electron transport component, the organic EL devices of the present invention can provide a number of improved performance characteristics, such as high luminance, low driving voltages, long device operation stability and extended useful durability, the enablement of light emission from about 400 nanometers to about 700 nanometers, and the use of a cathode comprised of a metal such as aluminum.

DESCRIPTION OF EMBODIMENTS

The electron transport materials selected for the organic EL devices of the present invention are comprised of, for example, the triazine compounds illustrated by the formula (I)

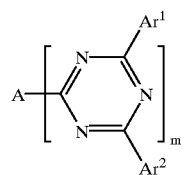

wherein $Ar^1$ and $Ar^2$ are independently an aliphatic group, an aryl group selected, for example, from the group consisting of a phenyl, a stilbenyl, a biphenylyl, a naphthyl, a pyridyl, and a quinolyl, and the like, or mixtures of aryl and aliphatic and wherein the aryl group may further contain a substituent selected from the group consisting of hydrogen, an alkyl group with for example, preferably from 1 to about 6 carbon atoms, an alkoxy group with, for example, preferably from 1 to about 6 carbon atoms, a dialkylamino group with preferably from about 1 to about 3 carbon atoms, a halogen, a cyano group and the like; m is a number of from 1 to about 4; wherein A is a monovalent or a multi-valent aromatic group which contains at least two conjugate-linked or two fused aromatic rings, and preferably is independently selected from the group consisting of

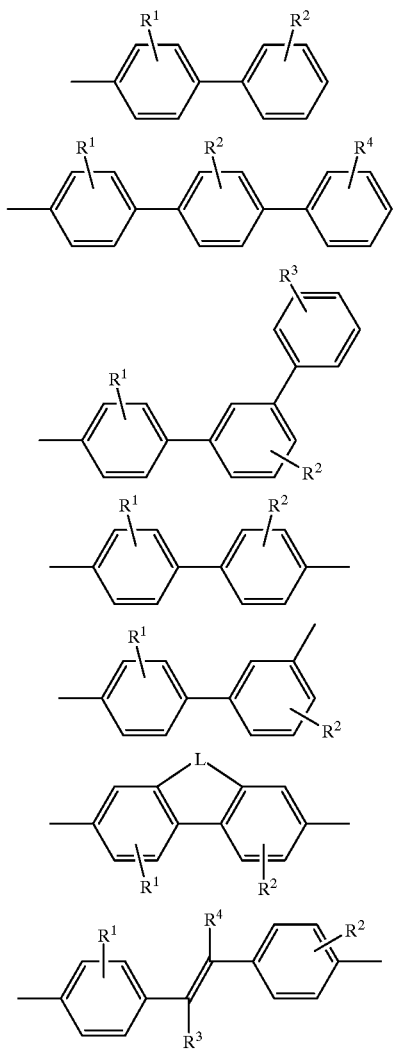

-continued

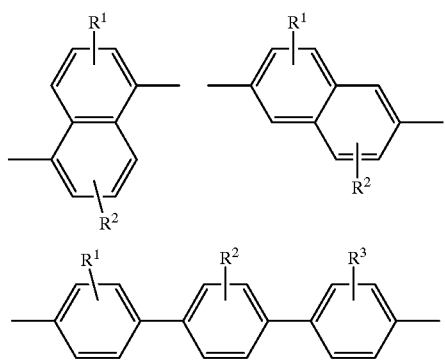

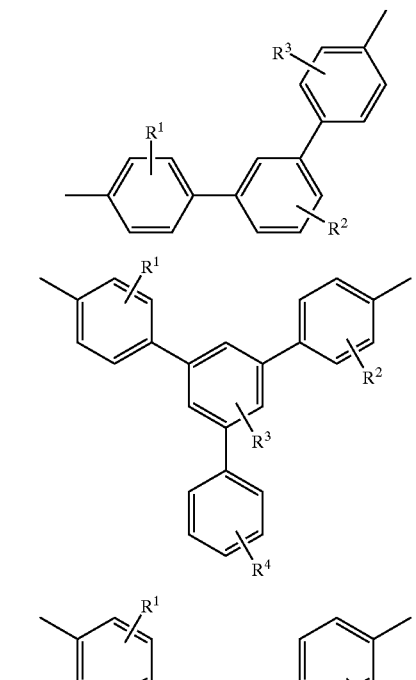

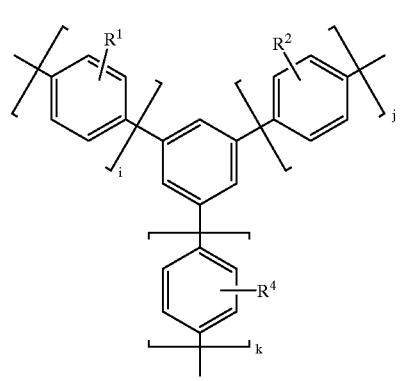

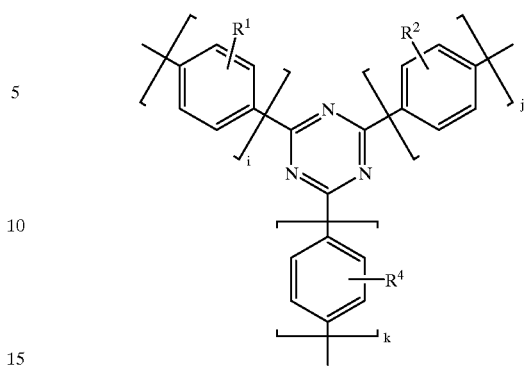

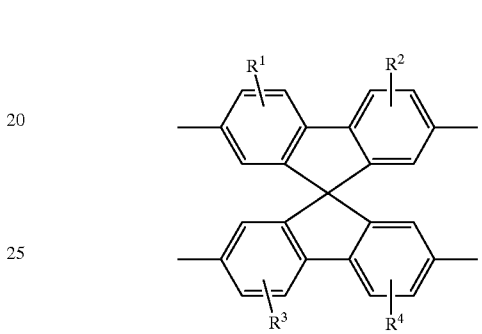

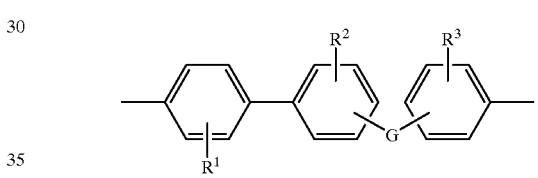

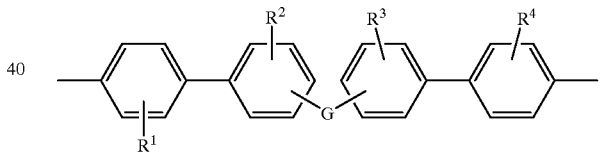

wherein $R^1$ to $R^5$ are each independently a substituent, preferably selected from the group consisting of hydrogen aliphatic such as an alkyl group, an alkoxy group, a halogen such as a chloride atom, a cyano group, and the like; L is a divalent group which may be selected from the group consisting of —C(R'R")—, an ethylene, —Si(R'R")—, an oxygen atom, a surfer atom, and the like, and preferably L is —C(R'R")—, wherein R' and R" is a hydrogen atom, an alkyl group containing from 1 to about 10 carbon atoms, or an alkoxyl group containing from 1 to about 10 carbon atoms, or an aryl; G is a divalent linkage, which may be selected from the group consisting of —C(R'R")—, an ethylene, —Si(R'R")—, an oxygen atom, a sulfur atom, and the like; preferably L is —C(R'R")—, wherein R' and R" is a hydrogen atom, an alkyl group containing from 1 to about 5 carbon atoms, an oxygen atom, or an aryl; and i, j, k are a number of from 1 to about 3.

Preferably, A is a monovalent or a multi-valent aromatic group which contains a biphenyl unit, a naphthalene unit, a stilbene unit, and the like; $Ar^1$ to $Ar^5$ are independently an aryl group selected from the group consisting of a phenyl, a stilbenyl, a biphenylyl, and a naphthyl, and wherein the aryl group contains a substituent selected from the group consisting of hydrogen, an alkyl group with, for example, preferably from 1 to about 6 carbon atoms, an alkoxy group with preferably from 1 to about 6 carbon atoms, a halogen, a cyano group and the like; more preferably $Ar^1$ to $Ar^5$ are each a phenyl, a tolyl, and a methoxyphenyl; $R^1$ to $R^5$ are each independently a substituent selected from the group consisting of hydrogen a methyl, a butyl, a methoxyl, and the like; L is a divalent group selected from the group consisting of —C(R'R")—, wherein R' and R" is a hydrogen atom, an alkyl group containing from 1 to about 10 carbon atoms, or an alkoxyl group containing from 1 to about 10 carbon atoms; G is a divalent linkage selected from the group consisting of —C(R'R")—, an oxygen atom, a sulfur atom, and the like.

A particularly preferred class of the components or compounds are illustrated by the following

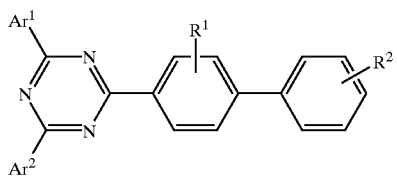

(II)

wherein $Ar^1$ and $Ar^2$ are each independently an aromatic, such as aryl with from 6 to about 30 carbon atoms, selected, for example, from the group consisting of a phenyl, a stilbenyl, a biphenylyl, a naphthyl, a pyridyl, and a quinolyl and the like, and preferably a phenyl and a naphthyl, and wherein the aryl group may further contain a substituent selected from the group consisting of hydrogen, an alkyl group with for example, from 1 to about 10 carbon atoms, an alkoxy group with, for example, from 1 to about 10 carbon atoms, a dialkylamino group with preferably from about 1 to about 3 carbon atoms, a halogen, a cyano group and the like; $R^1$ and $R^2$ are substituents selected from the group consisting of hydrogen, aliphatic such as an alkyl group, an alkoxy group, a halogen such as a chloride atom, a cyano group, and the like.

The electron transport, which may also function as electron injectors or can be considered an electron injector triazine compounds, can be prepared by standard synthetic processes. In an illustrative example, the triazines such as those of Formula (III) can be synthesized as follows: a mixture of one equivalent of a suitable dicarbonyl halide, especially chloride compound such as 4,4'-biphenyidicarbonyl chloride or 4,4'-stilbene dicarbonyl chloride, from about 4 to about 6 equivalents of the corresponding aromatic nitrile compounds such as benzonitrile, m-tolunitrile, p-tolunitrile and the like, from about 2 to about 5 equivalents of aluminum chloride, and suitable amounts of an inert solvent, such as an organic solvent like o-dichlorobenzene, is first heated to from about 120° C. to about 200° C., and preferably from about 1400C to about 160° C. for about a suitable percent, for example from about 0.1 to about 1, and preferably about 0.5 hour; from about 2 to about 5 equivalents of ammonium chloride are then added, and the resulting reaction mixture is stirred for about 15 hours, or other suitable time. After cooling to room temperature of about 23° C., the reaction contents are added to an alcohol like methanol or water, and the resulting precipitate is collected by filtration. The product may further be purified by standard purification means including recrystallization and sublimation. The triazine compound products obtained may be confirmed by elemental analysis, NMR or IR spectrometric identification techniques.

Specific examples of triazines compounds of Formula (II) include 2,4,6-tris(4-biphenylyl)-1,3,5-triazine (II-1), 2,4,6-tris[4-(4'-methylbiphenylyl)]-1,3,5-triazine (II-2), 2,4,6-tris[4-(4'-tert-butylbiphenylyl)-1,3,5-triazine (II-3), 2,4,6-tris[4-(3',4'-dimethylbiphenylyl)]-1, 3,5-triazine (II-4), 2,4,6-tris[4-(4'-methoxybiphenylyl)]-1,3,5-triazine (II-5), 2,4,6-tris[4-(3'-methoxybiphenylyl)]-1,3,5-triazine (II-6), 2,4-bis(4-biphenylyl)-6-phenyl-1,3,5-triazine (II-7), 2,4-bis(4-biphenylyl)-6-m-tolyl-1,3,5-triazine (II-8), and the like.

Specific examples of triazines compounds of formula (III) include 4,4'-bis-[2-(4,6-diphenyl-1,3,5-triazinyl)]-1,1'-biphenyl (III-1), 4,4'-bis-[2-(4,6-di-p-tolyl-1,3,5-triazinyl)]-1,1'-biphenyl (III-2), 4,4'-bis-[2-(4,6-di-m-tolyl-1,3,5-triazinyl)]-1,1'-biphenyl (III-3), 4,4'-bis-[2-(4,6-di-p-methoxyphenyl-1,3,5-triazi nyl)]-1,1 '-b iphenyl (III-4), 4,4'-bis-[2-(4,6-di-m-methoxyphenyl-1,3,5-triazinyl)]-1,1'-biphenyl (III-5), 4,4'-bis-[2-(4-β-naphthyl-6-phenyl-1,3,5-triazinyl)]-1,1'-biphenyl (III-6), 4,4'-bis-[2-(4,6-di-biphenylyl-1, 3,5-triazinyl)]-1,1'-biphenyl (III-7), 4-[2-(4, 6-d i-phenyl-1,3, 5-triazinyl)]-4'-[2-(4,6-di-m-tolyl-1,3,5-triazinyl)]-1,1'-biphenyl (III-7), and the like, and examples of triazines compounds of formula (IV) include 2,7-bis-[2-(4,6-di-phenyl-1,3,5-triazinyl)]fluorene (IV-1), 2,7-bis-[2-(4,6-di-phenyl-1,3,5-triazinyl)]-9,9-dimethylfluorene (IV-2), 2,7-bis-[2-(4,6-di-phenyl-1,3,5-triazinyl)]-9,9-diethylfluorene (IV-3), 2,7-bis-[2-(4,6-di-phenyl-1,3,5-triazinyl)]-9,9-diphenylfluorene (IV-4), 2,7-bis-[2-(4,6-di-phenyl-1,3,5-triazinyl)]-9,10-dihydraphenanthrene (IV-5), 4,9-bis-[2-(4,6-di-phenyl-1,3,5-triazinyl)]dibenzofuran (IV-6), 4,9-bis-[2-(4,6-di-phenyl-1,3,5-triazinyl)] dibenzothiophene (IV-7), 2,7-bis-[2-(4,6-di-phenyl-1,3,5-triazinyl)]-9,9-dimethyl-9-silafluorene (IV-8), and the like.

Specific examples of triazines compounds of Formula (V) include 4,4'-bis-[2-(4,6-di-phenyl-1,3,5-triazinyl)]-stilbene (V-1), 4,4'-bis-[2-(4-phenyl-6-m-tolyl-1,3,5-triazinyl)]-stilbene (V-2) 4,4'-bis-[2-(4,6-di-p-tolyl-1,3,5-triazinyl)]-stilbene (V-3), 4,4'-bis-[2-(4,6-di-m-tolyl-1,3,5-triazinyl)]-stilbene (V-4), 4,4'-bis-[2-(4,6-di-m-methoxyphenyl-1,3,5-triazinyl)]-stilbene (V-4), and the like.

II-1

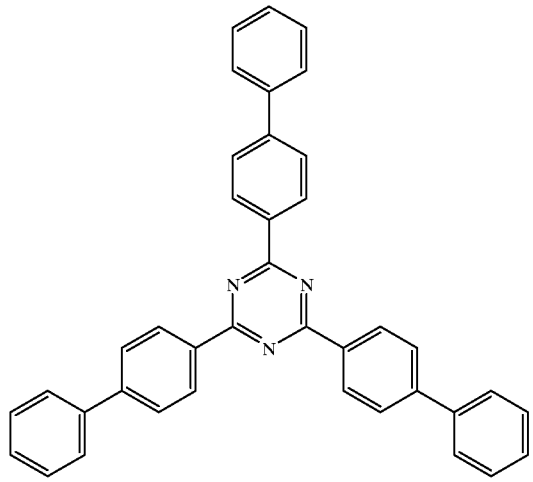

II-2
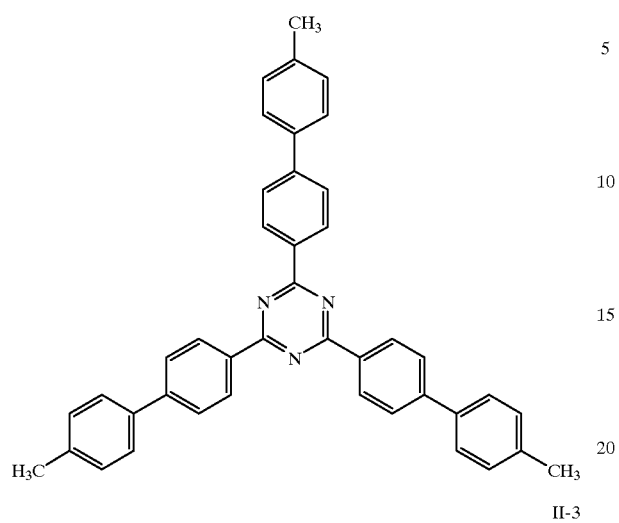
II-3
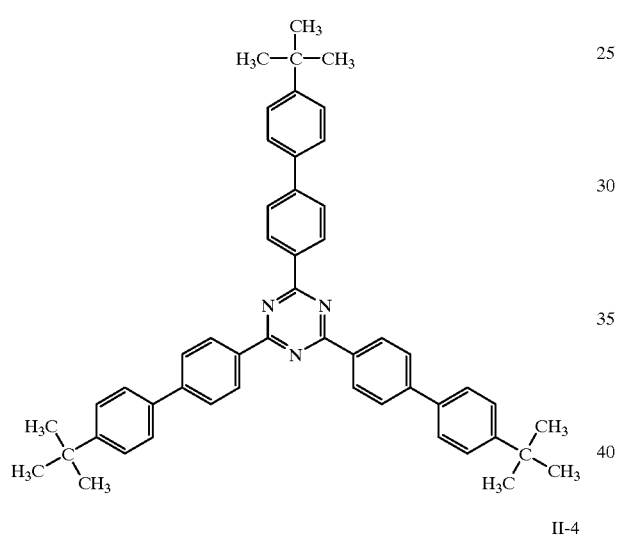
II-4
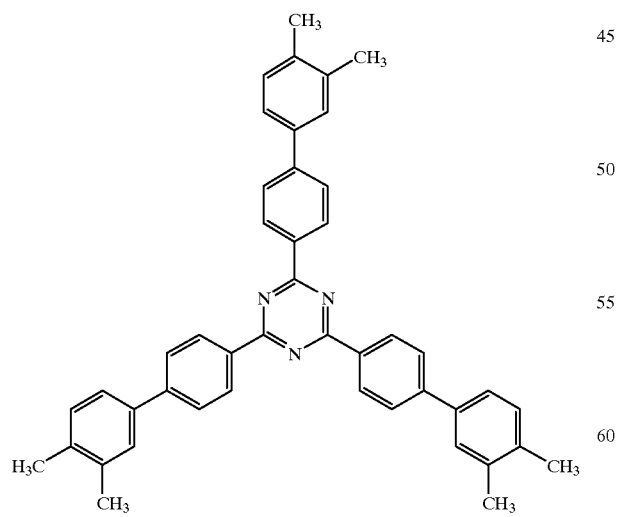
II-5
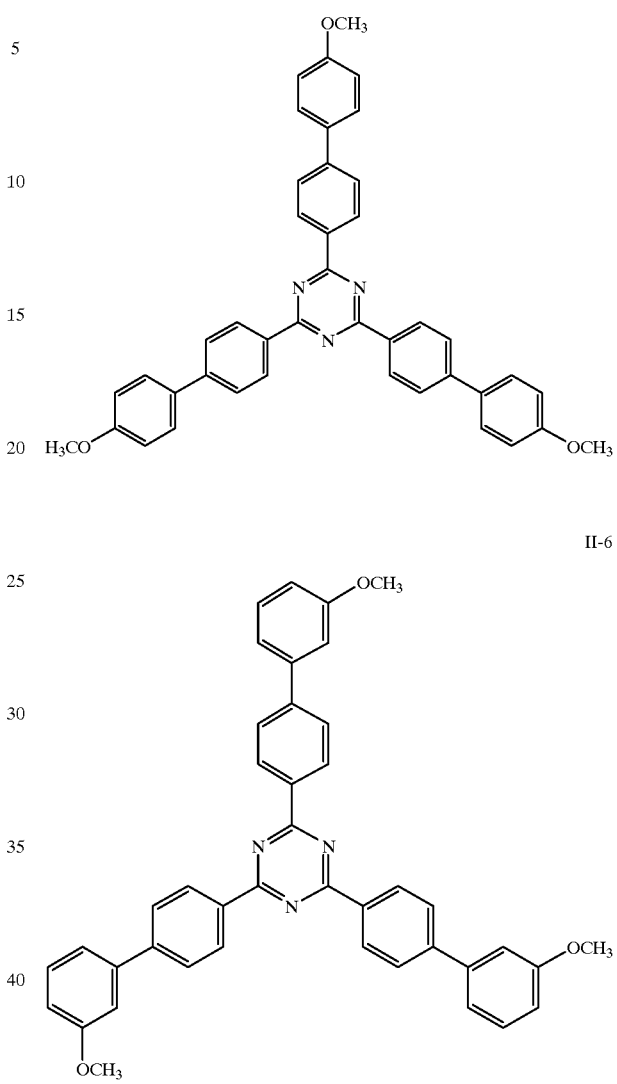
II-6
II-7
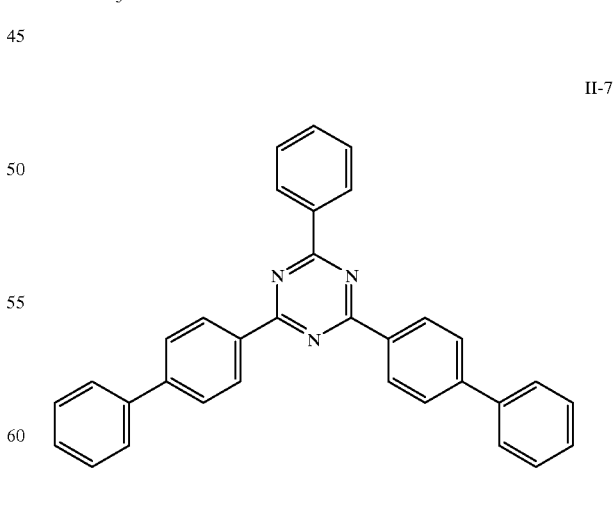

II-8
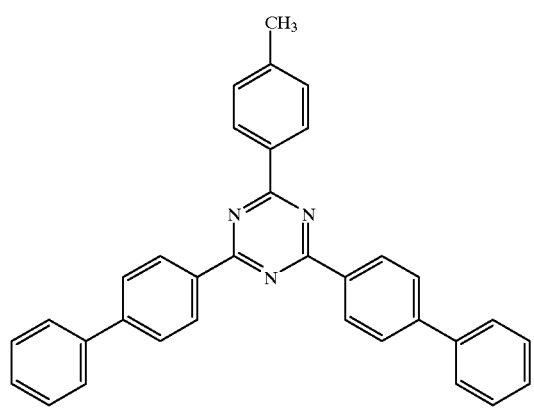
III-1
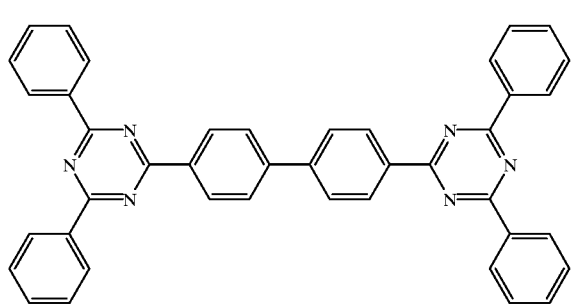
III-2
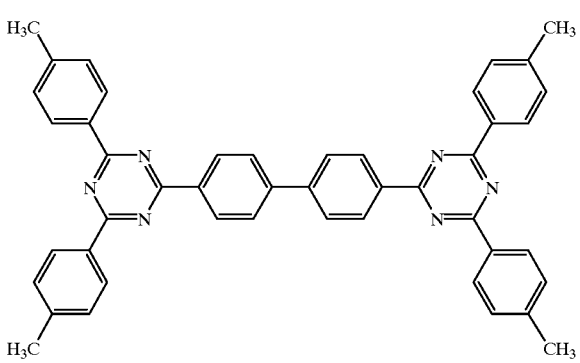
III-3
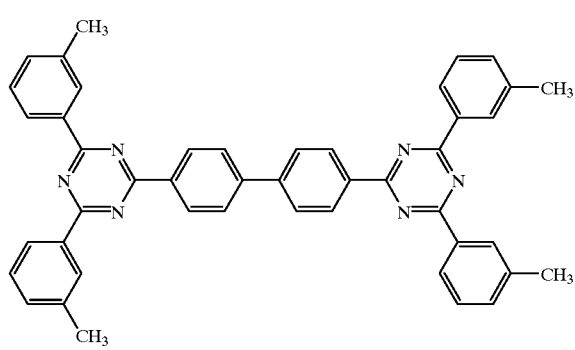
III-4
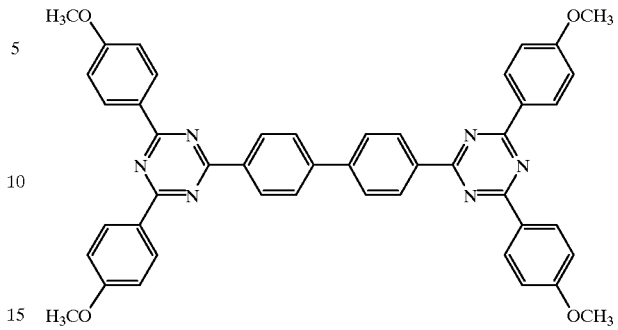
III-5
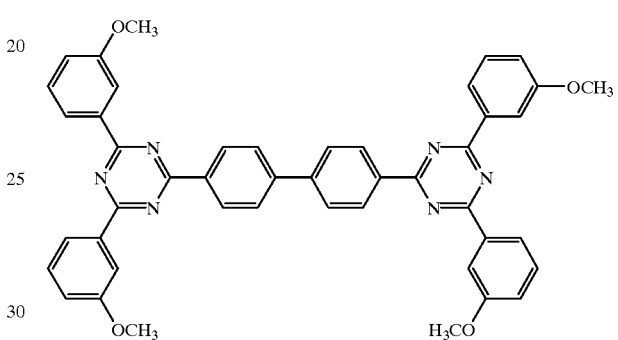
III-6
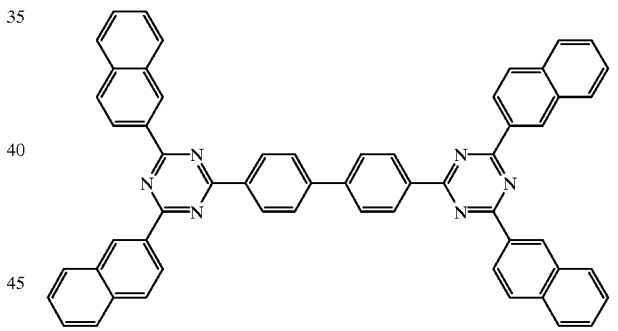
III-7
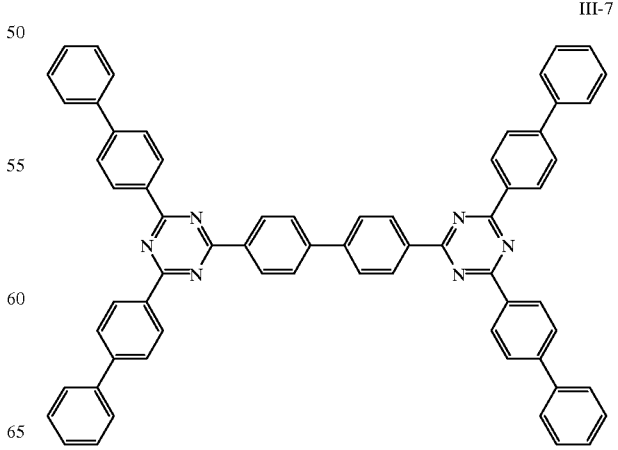

III-8
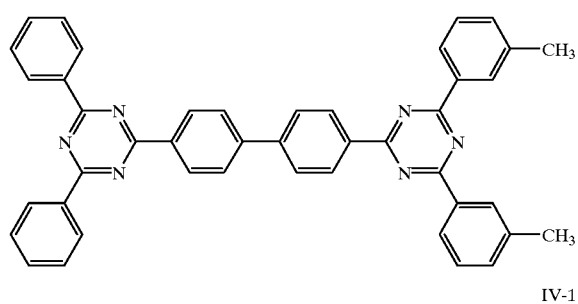
IV-1
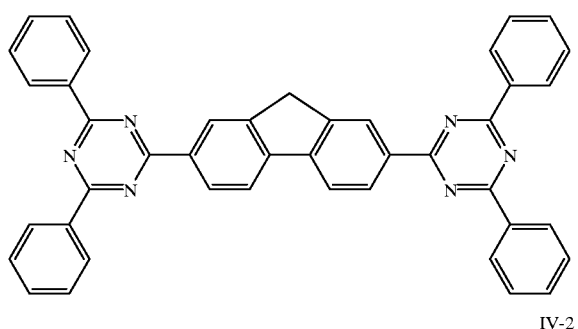
IV-2
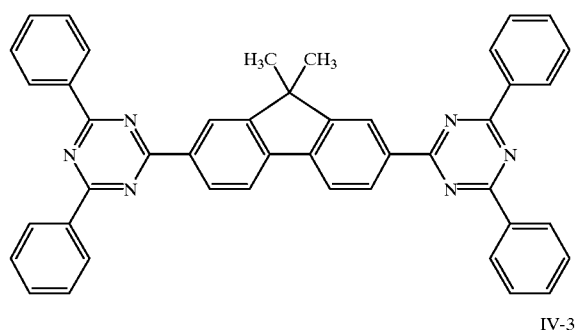
IV-3
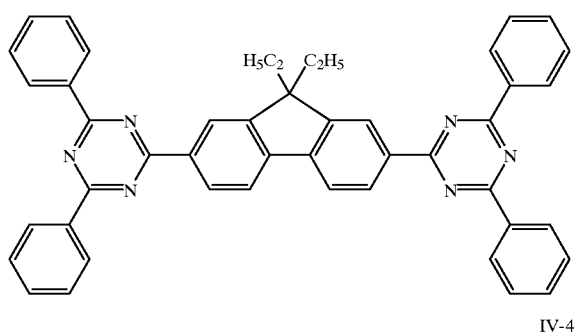
IV-4
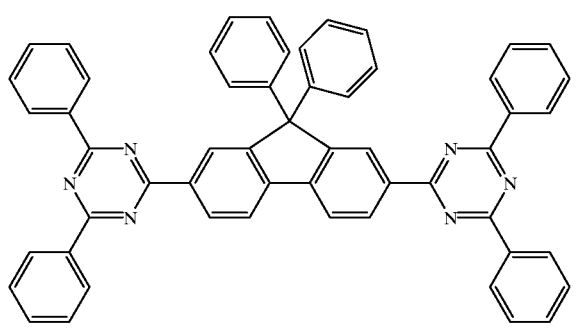
IV-5
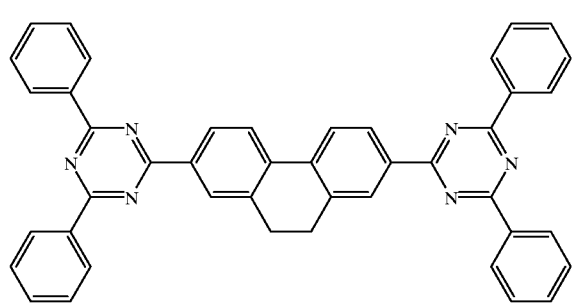
IV-6
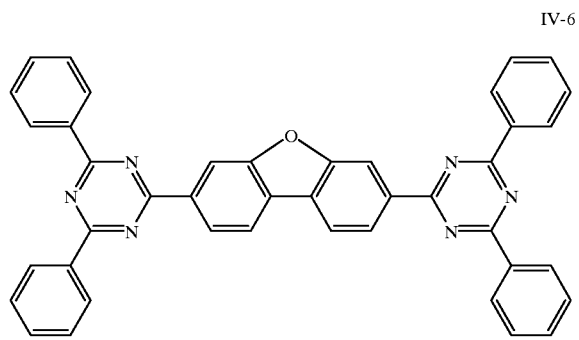
IV-7
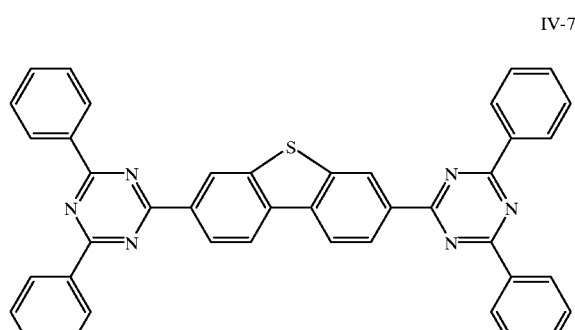
IV-8
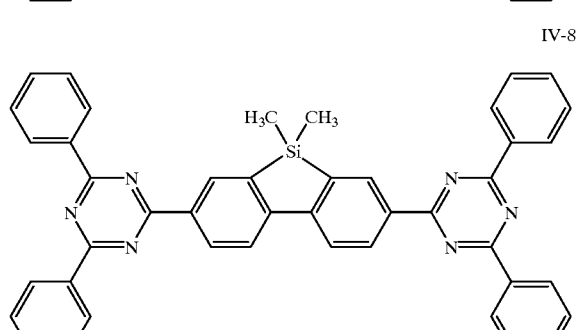
V-1
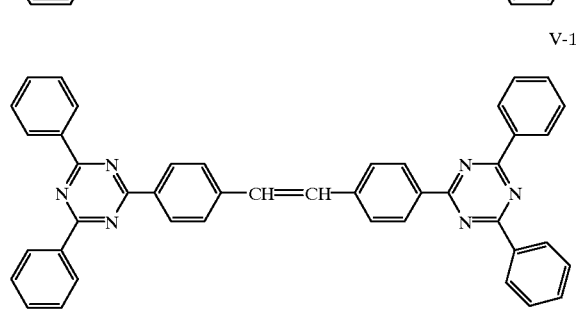

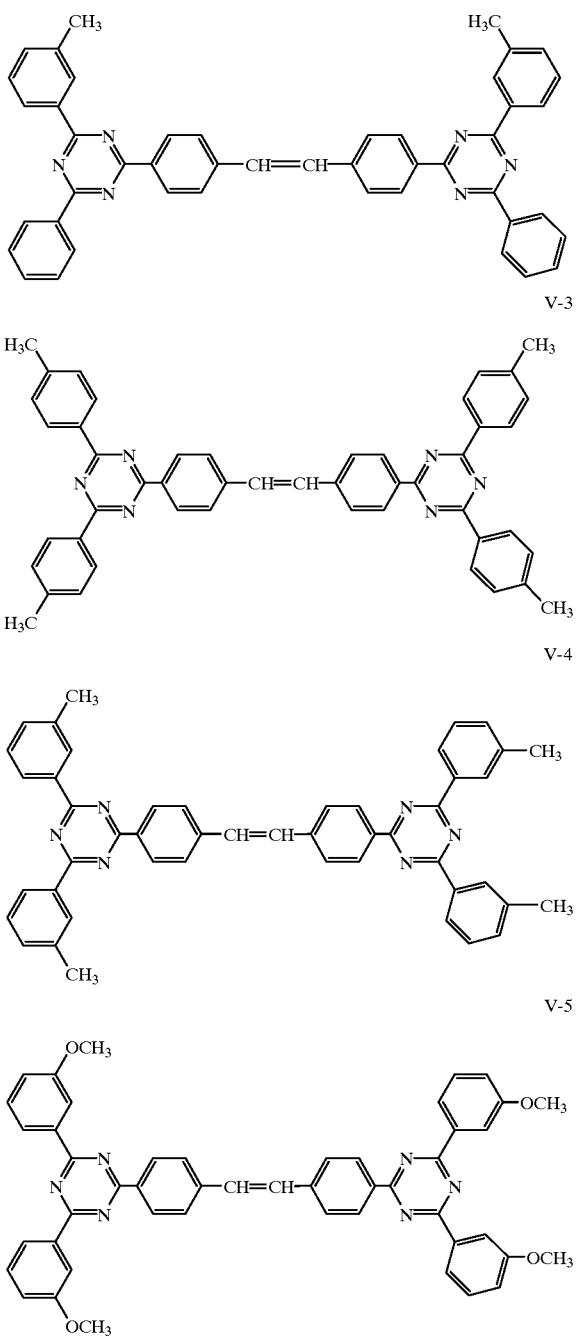

The EL devices or an organic light emitting diode of the present invention can be comprised of a supporting substrate of, for example, glass, an anode thereover of, for example, indium tin oxide in a thickness of from about 1 to about 500 nanometers and preferably from about 30 to about 100 nanometers (throughout the thickness ranges for each layer are examples and other suitable thickness may be selected), optionally a buffer layer in contact with the anode and comprised of a conductive component or hole transport materials in a thickness from about 5 to about 500 nanometers and preferably from about 10 to about 100 nanometers, an organic hole transporting layer thereover of, for example, 4,4'-bis-(9-carbazolyl)-1,1-biphenyl in a thickness of from about 1 to about 200 nanometers and preferably from about 5 to about 100 nanometers; an organic electron transport layer in contact with the hole transporting layer comprised of the triazine compounds of the formulas or encompassed by the formulas illustrated herein in a thickness of from about 5 to about 300 nanometers and preferably from about 10 to about 100 nanometers, and in contact therewith a low work function metal as a cathode. In this EL device, light emission may originate from the hole transport layer or the electron transport layer, either of which may optionally doped with a fluorescent dye when serves as light-emitting layer.

In an embodiment, the light emitting diode or EL device is comprised in sequence of a supporting substrate of, for example, glass, an anode of, for example, indium tin oxide in a thickness of from about 1 to about 500 nanometers, and preferably from about 30 to about 100 nanometers, a buffer layer of an aromatic amine compound in a thickness from about 5 to about 300 nanometers, and preferably from about 10 to about 100 nanometers, an organic hole transporting layer of, for example, N,N'-di-1-naphthyl-N,N'-diphenylbiphenyl4,4'-diamine in a thickness of from about 1 to about 200 nanometers, and preferably from about 5 to about 100 nanometers, an organic light emitting layer comprised of, for example, tris-(8-hydroxyquinolinato) aluminum, optionally doped with a fluorescent dye, and which layer is of a thickness of from about 5 to about 300 nanometers, and preferably from about 10 to about 100 nanometers, an organic electron transporting layer comprised of the triazine compounds of the formulas or encompassed by the formulas illustrated herein in a thickness of from about to about 300 nanometers and preferably from about 10 to about 100 nanometers, and in contact therewith a low work function metal cathode.

In aspects thereof, the present invention relates to electroluminescent devices comprised of an anode, a hole transporting layer, an electron transport layer, and a cathode, wherein the electron transport layer serves as a light emitting layer, which layer contains a triazine component of Formulas I, II, III, IV, or V, and preferably the triazine compounds of Formulas III, IV or V; an electroluminescent device wherein the electron transporting layer serves as a light-emitting layer; an electroluminescent device wherein the hole transporting layer serves as a light-emitting layer; an electroluminescent device wherein the hole transporting layer is comprised of a tertiary aromatic amine; an electroluminescent device wherein the hole transporting layer is comprised of a N,N,N',N'-tetraaylbenzidine compound; an electroluminescent device wherein a buffer layer is further included between the anode and the hole transporting layer; an electroluminescent device wherein the buffer layer is comprised of a mixture of a tertiary aromatic amine and an aromatic polycyclic hydrocarbon stabilizer, wherein the stabilizer is optionally present in a concentration of from about 0.5 to about 10 weight percent, based on the weight of the tertiary aromatic amine; an electroluminescent device wherein the tertiary aromatic amine is N,N'-di-1-naphthyl-N,N'-diphenyl-benzidine and the polycyclic hydrocarbon stabilizer is rubrene or 9,10-diphenylanthracene; an electroluminescent device further comprised of a light-emitting layer positioned between the hole transport layer and the electron transport layer; an electroluminescent device wherein the light-emitting layer is comprised of a metal chelate compound of an 8-hydroxyquinoline compound; an electroluminescent device wherein the light-emitting layer is comprised of tri-(8-hydroxyquinolinato)aluminum; an electroluminescent device wherein the light-emitting layer is comprised of tri-(8-hydroxyquinolinato)aluminum; an electroluminescent device wherein the light-emitting layer is comprised of a stilbene compound; an electroluminescent device wherein the light-emitting layer is comprised of 4,4'-bis(2,2-diphenylvinyl)biphenyl, and an EL device containing as the triazine compounds of the electron transport layer 2,4,6-tris(4-biphenylyl)-1,3,5-triazine, 2,4,6-tris[4-(4'-methylbiphenylyl)]-1,3,5-triazine, 2,4,6-tris[4-(4'-tert-butylbiphenylyl)-1,3,5-triazine, 2,4,6-tris[4-(4'-methoxybiphenylyl)]-1,3,5-triazine, 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-m-methoxyphenyl-1,3,5-triazinyl)]-1,1'-biphenyl, 4,4'-bis-[2-(4-β-naphthyl-6-phenyl-1,3,5-triazinyl)]-1,1'-biphenyl, 2,7-bis-[2-(4,6-di-phenyl-1,3,5-triazinyl)]fluorene, 2,7-bis-[2-(4,6-di-phenyl-1,3,5-triazinyl)]-9,9-dimethylfluorene, 4,4'-bis-[2-(4,6-di-phenyl-1,3,5-triazinyl)]-stilbene, 4,4'-bis-[2-(4-phenyl-6-m-tolyl-1,3,5-triazinyl)]-stilbene, and the like.

The electroluminescent device of the present invention can comprise a light-emitting layer, which layer may be encompassed within the hole transport layer or the electron transport layer. The light emitting layer may be an independent layer positioned between the hole transport layer and the triazine electron transport layer, preferably those with strong fluorescence such as the triazines of Formulas III, IV, or V. Illustrative examples of fluorescent triazine compounds include 4,4'-bis-[2-(4,6-diphenyl- 1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-m-methoxyphenyl-1,3,5-triazinyl)]-1,1'-biphenyl, 4,4'-bis-[2-(4-0-naphthyl-6-phenyl-1,3,5-triazinyl)]-1,1'-biphenyl, 2,7-bis-[2-(4,6-di-phenyl-1,3,5-triazinyl)]fluorene, 2,7-bis-[2-(4,6-di-phenyl-1,3,5-triazinyl)]-9,9-dimethylfluorene, 4,4'-bis-[2-(4,6-d i-phenyl-1,3,5-triazinyl)]-stilbene, 4,4'-bis-[2-(4-phenyl-6-m-tolyl-1,3,5-triazinyl)]-stilbene, and the like.

Examples of luminescent materials for forming the light-emitting layer includes the metal chelates of 8-hydroxyquinoline as disclosed in U.S. Pat. Nos. 4,539,507; 5,151,629; and 5,150,006, the disclosures of which are totally incorporated herein by reference. Illustrative specific examples of luminescent materials or compounds include tris(8-hydroxyquinolinate) aluminum, a preferred one, tris (8-hydroxyquinolinate) gallium, bis(8-hydroxyquinolinate) magnesium, bis(8-hydroxyquinolinate) zinc, tris(5-methyl-8-hydroxyquinolinate) aluminum, tris(7-propyl-8-quinolinolato) aluminum, bis[benzo{f}-8-quinolinate]zinc, bis(10-hydroxybenzo[h]quinolinate) beryllium, and the like. Also, another preferred class of luminescent materials include butadienes, such as 1,4-diphenylbutadiene and tetraphenylbutadiene, and stilbenes, and the like as illustrated in U.S. Pat. Nos. 4,356,429 and 5,516,577, the disclosures of which are totally incorporated herein by reference.

The light emitting layer, which may be encompassed with the hole transport layer or the electron transport layer, may further contain a fluorescent dye capable of emitting light in response to hole-electron recombination thereby enabling improved device performance characteristics, such as excellent emission hue and desirable electroluminescent efficiency. The fluorescent component is present in, for example, from about 0.01 to about 10 weight percent, and preferably from about 1 to about 5 weight percent of the layer. Illustrative examples of fluorescent components include dyes selected, for example, from the group consisting of coumarin, dicyanomethylene pyranes, polymethine, oxabenzanthrane, xanthene, pyrylium, carbostyl, perylene, and the like; a dye selected from the group consisting of quinacridone derivatives. Illustrative examples of quinacridone dyes include quinacridone, 2-methylquinacridone, 2,9-dimethylquinacridone, 2-chloroquinacridone, 2-fluoroquinacridone, 1,2-benzoquinacridone, N,N'-dimethylquinacridone, N,N'-dimethyl-2-methylquinacridone, N,N'-dimethyl-2,9-dimethylquinacridone, N,N'-dimethyl-2-chloroquinacridone, N,N '-d imethyl-2-fluoroquinacridone, N,N'-dimethyl-1,2-benzoquinacridone, and the like. A preferred class of fluorescent materials are fused ring fluorescent dyes, examples of which are perylene, rubrene, anthracene, coronene, phenanthrecene, pyrene and the like, as illustrated in U.S. Pat. No. 3,172,862, the disclosure of which is totally incorporated herein by reference. Also, fluorescent materials that can be used as a dopant include butadienes, such as 1,4-diphenylbutadiene and tetraphenylbutadiene, and stilbenes, and the like as illustrated in U.S. Pat. Nos. 4,356,429 and 5,516,577, the disclosures of which are totally incorporated herein by reference.

It is desirable that the organic EL devices of the present invention comprise a supporting substrate. Illustrative examples of supporting substrates include polymeric components, glass and the like, and polyesters like MYLAR®, polycarbonates, polyacrylates, polymethacrylates, polysulfones, quartz, and the like. Other substrates can also be selected provided, for example, it can effectively support the other layers, and that it does not interfere with the device functional performance. The thickness of the substrate can be, for example, from about 25 to about 1,000 microns or more, and, for example, from about 50 to about 500 microns depending, for example on the structural demands of the device.

Examples of the anode which is contiguous to the substrate, include positive charge injecting electrodes such as indium tin oxide, tin oxide, gold, platinum, or other suitable materials such as electrically conductive carbon, π-conjugated polymers such as polyaniline, polypyrrole, and the like with, for example, a work function equal to, or greater than about 4 electron volts, and more specifically, from about 4 to about 6 electron volts. The thickness of the anode can range from about 1 to about 500 nanometers with the preferred range being dictated by the optical constants of the anode material. One preferred range of anode thickness is from about 30 to about 100 nanometers.

The buffer layer, which primarily functions to facilitate efficient injection of holes from the anode, and to improve the adhesion between the anode and the organic hole transporting layer, thus further improving the device operation stability includes conductive materials such as polyaniline and its acid-doped forms, polypyrrole, poly(phenylene vinylene), and known semiconductive organic materials; porphyrin derivatives disclosed in U.S. Pat. No. 4,356,429, the disclosure of which is totally incorporated herein by reference, such as 1,10,15,20-tetraphenyl-21H,23H-porphyrin copper (II); copper phthalocyanine, copper tetramethyl phthalocyanine; zinc phthalocyanine; titanium oxide phthalocyanine; magnesium phthalocyanine; and the like.

A preferred class of hole transporting materials that can be selected for the buffer layer are the aromatic tertiary amines such as those disclosed in U.S. Pat. No. 4,539,507, the disclosure of which is totally incorporated herein by reference. Representative examples of aromatic tertiary amines are bis(4-dimethylamino-2-methylphenyl)phenylmethane, N,N,N-tri(p-tolyl)amine, 1,1-bis(4-di-p-tolylaminophenyl) cyclohexane, 1,1-bis(4-di-p-tolylaminophenyl)-4-phenyl cyclohexane, N,N'-diphenyl-N,N'-bis(3-methylphenyl)-1,1'-biphenyl-4,4'-diamine, N,N'-diphenyl-N,N'-bis(3-methylphenyl)-1,1'-biphenyl-4,4'-diamine, N,N'-diphenyl-N,N'-bis(4-methoxyphenyl)-1,1'-biphenyl4,4'-diamine, N,N,N',N'-tetra-p-tolyl-1,1'-biphenyl-4,4'-diamine, N,N'-di-1-naphthyl-N,N'-diphenyl-1,1'-biphenyl-4,4'-diamine, and the like. Another class of aromatic tertiary amines selected for the hole transporting layer is polynuclear aromatic amines, such as N,N-bis-[4'-(N-phenyl-N-m-tolylamino)-4-biphenylyl]aniline; N,N-bis-[4'-(N-phenyl-N-m-tolylamino)-4-biphenylyl]-m-toluidine; N,N-bis-[4'-(N-phenyl-N-m-tolylamino)-4-biphenylyl]-p-toluidine; N,N-bis-[4'-(N-phenyl-N-p-tolylamino)4-biphenylyl]aniline; N,N-bis-[4'-(N-phenyl-N-p-tolylamino)-4-biphenylyl]-m-toluidine; N,N-bis-[4'-(N-phenyl-N-p-tolylamino)-4-biphenylyl]-p-toluidine; N,N-bis-[4'-(N-phenyl-N-p-chlorophenylamino)-4-biphenylyi]-m-toluidine; N,N-bis-[4'-(N-phenyl-N-m-chlorophenylamino)-4-biphenylyl]-m-toluidine; N,N-bis-[4'-(N-phenyl-N-m-chlorophenylamino)-4-biphenylyl]-p-toluidine; N,N-bis-[4'-(N-phenyl-N-m-tolylamino)-4-biphenylyl]-p-chloroaniline; N,N-bis-[4'-(N-phenyl-N-p-tolylamino)-4-biphenylyl]-m-chloroaniline; N,N-bis-[4'-(N-phenyl-N-m-tolylamino)-4-biphenylyl]-1-aminonaphthalene and the like.

The buffer layer can be comprised of aromatic tertiary amines and which layer may further include a stabilizer as disclosed in U.S. Pat. No. 5,846,666, the disclosure of which is totally incorporated herein by reference, a stabilizer comprised of certain hydrocarbon compounds such as rubrene, 4,8-diphenylanthrecene, and the like. The buffer layer can be prepared by forming one of the above compounds into thin film by known methods, such as vapor deposition or spin coating. The thickness of buffer layer thus formed is not particularly limited, and can be in a range of from about 5 nanometers to about 300 nanometers, and preferably from about 10 nanometers to about 100 nanometers.

The hole transporting layer can be comprised of a hole transporting material with a thickness ranging from about 1 nanometer to about 200 nanometers, and preferably from about 5 nanometers to about 100 nanometers. Any conventional suitable aromatic amine hole transporting materials described for the buffer layer may also be selected for forming this layer.

A preferred class of hole transporting materials selected for forming the hole transporting layer is 4,4'-bis(9-carbazolyl)-1,1'-biphenyl compounds. Illustrative examples of 4,4'-bis(9-carbazolyl)-1,1'-biphenyl compounds include 4,4'-bis(9-carbazolyl)-1,1'-biphenyl and 4,4'-bis(3-methyl-9-carbazolyl)-1,1'-biphenyl, and the like.

The cathode can be comprised of any suitable material such as a metal, including high, for example from about 4.0 eV to about 6.0 eV, or low work function component, such as metals with, for example, an eV of from about 2.5 eV to about 4.0 eV (electron volts). The cathode can be derived from a combination of a low work function metal (about 4 eV, for example from about 2 to about 4 eV) and at least one other metal. Effective proportions of the low work function metal to the second or one other metal are from less than about 0.1 percent to about 99.9 percent by weight. Illustrative examples of low work function metals include alkaline metals such as lithium or sodium, Group 2A or alkaline earth metals such as beryllium, magnesium, calcium, or barium, and Group III metals including rare earth metals and the actinide group metals such as scandium, yttrium, lanthanum, cerium, europium, terbium, or actinium. Lithium, magnesium and calcium are preferred low work function metals.

The thickness of cathode ranges from, for example, about 10 nanometers to about 500 nanometers. The Mg:Ag cathodes of U.S. Pat. No. 4,885,211, the disclosure of which is totally incorporated herein by reference, constitute one preferred cathode construction. Another preferred cathode described in U.S. Pat. No. 5,429,884, the disclosure of which are totally incorporated herein by reference, wherein the cathodes are formed from lithium alloys with other high work function metals such as aluminum and indium.

Both the anode and the cathode of the EL devices of the present invention may contain a protective coating thereon, and the anode and cathode can be of any convenient forms. A thin conductive layer can be coated onto a light transmissive substrate, for example a transparent or substantially transparent glass plate or plastic film. The EL device can include a light transmissive anode formed from tin oxide or indium tin oxide coated on a glass plate. Also, very thin, for example less than about 200 Å, and more specifically, from about 75 to about 150 Angstroms, light-transparent metallic anodes can be used, such as gold, palladium, and the like. In addition, transparent or semitransparent thin layers, for example from 50 to about 175 Angstroms of conductive carbon or conjugated polymers such as polyaniline, polypyrrole, and the like can be selected as anodes. Any light transmissive polymeric film can be employed as the substrate. Additional suitable forms of the anode and cathode are illustrated in U.S. Pat. No. 4,885,211, the disclosure of which is totally incorporated herein by reference.

Aromatic refers, for example, to aryl, such as phenyl, and which aryl can contain, for example, from about 6 to about 72 carbon atoms; aliphatic refers, for example, to alkyl, and alkoxy, each with from about 1 to about 40, preferably about 25, and most preferably from about 1 to about 6 carbon atoms; halogen refers, for example, to chloride, bromide, fluoride or iodide, and m is preferably from about zero (0) to about 3.

The following Examples are provided to further illustrate various species of the present invention, it being noted that these Examples are intended to illustrate and not limit the scope of the present invention.

EXAMPLE I

Synthesis of 4,4'-Bis-[2-(4,6-diphenyl-1,3,5-triazinyl)]-1,1'-biphenyl:

In a 100 milliliter round bottom flask there was added 4,4'-biphenyldicarbonyl chloride (5.14 grams), 1,2-dichlorobenzene (150 milliliters), thionyl chloride (2.0 milliliters), and aluminum chloride (5.5 grams) with stirring, and benzonitrile (7.6 grams) was added slowly; and the resulting reaction mixture was heated under argon to about 150° C. for 0.5 hour. The temperature of the reaction mixture was reduced to 120° C., then ammonium chloride (3.5 grams) was added in one portion. The reaction mixture resulting was stirred at 150° C. for an additional 20 hours. The reaction flask was removed from the heater and cooled to room temperature, about 25° C. throughout. The resulting mixture was poured into 600 milliliters of methanol and stirred for 20 minutes, and the precipitates were collected by filtration and dried in a vacuum oven to afford 2.7 grams of crude product which was further purified by sublimation. The above about 99 percent pure triazinyl product had a melting point of 362° C. IR (KBr): 1588, 1564, 1525, 1445,1368, 842, 827, 765, 690,645 cm$^{-1}$.

H-NMR (CDCl$_3$—CF3COOD): δ 7.76 (t, J=7.8 Hz), 7.92 (t, J=7.8 Hz), 8.10 (d, J=8.6 Hz), 8.63 (d, J=8.4 Hz), 8.84 (d, J=8.6 Hz).

$^{13}$-NMR(CDCl$_3$—CF3COOD): δ 129.1,129.3, 130.3, 130.4, 130.9, 131.9, 137.8, 147.8, 169.1, 169.4.

EXAMPLE II

Synthesis of 4.4'-Bis-[2-(4,6-di-p-tolyl-1,3,5-triazinyl)]-1,1'-biphenyl:

In a 250 milliliter round bottom flask there was added 4,4'-biphenyldicarbonyl chloride (8.215 grams), 1,2-dichlorobenzene (65 milliliters), thionyl chloride (1.0 milliliter), and aluminum chloride (7.3 grams). With stirring, p-tolunitrile (13.5 grams) was added slowly, and the resulting reaction mixture was heated under argon to about 150° C. for 0.5 hour. The temperature of the reaction mixture was reduced to 150° C., then ammonium chloride (7.13 grams) was added in one portion. The reaction mixture was stirred at this temperature for an additional 20 hours. The reaction flask was removed from the heater and cooled to room temperature. The mixture was poured into 600 milliliters of methanol and stirred for 20 minutes. The precipitates were collected by filtration and dried in a vacuum oven to afford 3.49 grams of crude product which was further purified by sublimation. The pure about 99.5 triazinyl product had a melting point of 427° C. IR (KBr): 1609,1585,1526,1406, 1369, 847, 800, 657, 582 cm$^{-1}$.

H-NMR (CDCl$_3$—CF3COOD): δ 2.53 (s), 7.55 (d, J=8.4 Hz), 8.06 (d, J=8.6 Hz), 8.52 (d, J=8.4 Hz), 8.79 (d, J=8.6 Hz).

$^{13}$C-NMR(CDCl$_3$—CF3COOD): δ 22.0, 126.5, 129.0, 130.6, 130.9, 131.1, 131.7, 147.5, 147.7, 150.6, 168.3, 169.2.

EXAMPLE III

Synthesis of 4.4'-Bis-[2-(4.6-di-m-tolyl-1,3,5-triazinyl)]-1,1'-biphenyl:

In a 200 milliliter round bottom flask there was added 4,4'-biphenyldicarbonyl chloride (8.0 grams), 1,2-dichlorobenzene (65.0 milliliters), thionyl chloride (1.6 milliliters), and aluminum chloride (7.6 grams). With stirring, m-tolunitrile (13.4 grams) was added slowly, and the resulting reaction mixture was heated under argon to about 150° C. for 0.5 hour. The temperature of the reaction mixture was reduced to 120° C., then ammonium chloride (6.1 grams) was added in one portion. The reaction mixture was stirred at 150° C. for additional 20 hours. The reaction flask was removed from the heater and cooled to room temperature, about 25° C. throughout. The resulting mixture was poured into 100 milliliters of methanol and stirred for 20 minutes. The precipitates were collected by filtration and dried in a vacuum oven to afford 2.568 grams of crude product which was further purified by sublimation. The pure 99.25 percent triazinyl product had a melting point of 343° C. IR (KBr): 1608, 1566, 1527, 1486, 1353, 828, 780, 769, 697, 676, 647 cm$^{-1}$.

H-NMR (CDCl$_3$—CF3COOD): δ 2.57 (s), 7.60~7.78 (m), 8.10 (d, J=8.6 Hz), 8.41(s), 8.85 (d, J=8.6 Hz).

$^{13}$C-NMR(CDCl$_3$—CF3COOD): δ 21.0, 128.1, 129.0, 129.2, 130.2, 130.7, 131.0, 131.9, 138.8, 140.9, 147.7, 168.8, 169.8.

EXAMPLE IV

Synthesis of 2,4,6-tris-(4-biphenylyl)-1,3,5-triazine:

In a 100 milliliter round bottom flask there was added 4-biphenylcarbonyl chloride (2.167 grams), 1,2-dichlorobenzene (27.0 milliliters), thionyl chloride (1.0 milliliter), and aluminum chloride (1.33 grams). With stirring, 4-biphenylcarbonitrile (3.58 grams) was added slowly, and the resulting reaction mixture was heated under argon to about 150° C. for 0.5 hour. The temperature of the reaction mixture was reduced to 120° C., then ammonium chloride (1.07 grams) was added in one portion. The reaction mixture was stirred at 150° C. for an additional 20 hours. The reaction flask was removed from the heater and cooled to room temperature, about 25° C. throughout. The resulting mixture was poured into 100 milliliters of methanol and stirred for 20 minutes. The precipitates were collected by filtration and dried in a vacuum oven to afford 3.9 grams of crude product which was further purified by sublimation. The above titled triazinyl product 2,4,6-tris-(4-biphenylyl)-1,3,5-triazine possessed a melting point of 283° C.

H-NMR (CDCl$_3$): δ 7.39~7.75 (m), 7.81 (d, J=8.7 Hz), 8.85 (d, J=8.7 Hz).

$^{13}$C-NMR(CDCl$_3$): δ 127.68, 127.72, 128.38, 129.32, 129.88, 135.61, 140.81, 145.57, 171.75.

EXAMPLE V

Synthesis of 4,4'-Bis-[2-(4,6-diphenyl-1,3,5-triazinyl)]-stilbene:

Caution: This reaction should be conducted in an efficient fume hood!

In a 100 milliliter round bottom flask, equipped with a condenser which was connected to an argon gas flow leading to a bleach solution, there was added 2,4-diphenyl-6-p-tolyl-1,3,5-triazine (12.477 grams) and sulfur powder (1.240 grams), and the resulting reaction mixture was then heated at 270° C. for 3 hours. The flask was removed from the heater, and 1,2-dichlorobenzene (68 milliliters) was added before the reaction mixture solidified. The solution was then poured into 500 milliliters of methanol. The precipitates were collected by filtration and dried in an oven to afford 11.514 grams of crude product which was purified by sublimation. The pure product, about 98 to 99 percent pure, had a melting point of 3900C. IR (KBr): 1604,1588,1526, 1446, 1368, 772, 741, 691 cm$^{-1}$.

H-NMR (CDCl$_3$—CF3COOD): δ 7.56 (s), 7.74 (t, J=7.8 Hz), 7.89–7.98 (m), 8.62 (d, J=8.0 Hz), 8.72 (d, J=8.6 Hz).

$^{13}$C-NMR(CDCl$_3$—CF3COOD): δ 128.6, 129.4, 129.5, 130.2, 130.8, 131.7, 132.4, 137.7, 145.7, 168.9, 169.0.

EXAMPLE VI

Organic EL Devices were Fabricated in the Following Manner:

1. A 500 Å indium tin oxide (ITO) anode coated glass substrate was selected, the thickness of the glass substrate being about 1 millimeter. The glass was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber, and a buffer layer was applied. The buffer layer deposition rate and layer thickness were controlled by an Inficon Model IC/5 controller. Under a pressure of about 5×10$^{-6}$ Torr, a 50 nanometers thick buffer was deposited on the ITO glass substrate through simultaneous evaporation of N,N'-1-naphthyl-N,N'-diphenyl-1,1'-biphenyl-4,4'-diamine at a rate of 0.6 nanometer/second and 5,10-diphenylanthracene at a rate of 0.03 nanometer/second from two independently controlled tantalum boats.

3. Onto the buffer layer was deposited a 30 nanometer hole transporting compound of 4,4'-bis(9-carbazolyl)-1,1'-biphenyl at a rate of 0.6 nanometer/second to form a 30 nanometers hole transporting layer.

4. A 50 nanometers thick light electron transport emitting layer was then deposited by evaporation of the triazines of Examples I to V, such as 4,4'-bis-[2-(4,6-diphenyl-1,3,5-triazinyl)]-1,1'-biphenyl, at a rate of 0.6 nanometer/second.

5. A 100 nanometer cathode of a magnesium silver alloy was deposited at a total deposition rate of 0.5 nanometer/second onto the light emitting layer above by the simultaneous evaporation from two independently controlled tantalum boats containing Mg and Ag, respectively. A typical composition was 9:1 in atomic ratio of Mg to Ag. Finally, a 200 nanometer silver layer was overcoated on the Mg:Ag cathode for the primary purpose of protecting the reactive Mg from ambient moisture.

The above EL device was retained in a dry box, which was continuously purged with nitrogen gas, and the performance thereof was assessed by measuring the current-voltage characteristics and light output under a direct current measurement. The current-voltage characteristics were determined with a Keithley Model 238 High Current Source Measure Unit. The ITO electrode was connected to the positive terminal of the current source. At the same time, the light output from the device was monitored by a silicon photodiode.

The light output from the above organic EL devices was 350 cd/m² when it was driven by a direct bias voltage of 8.5 volts. The EL color was blue with CIE color coordinates of X=0.147 and Y=0.099 measured by Minolta Chromameter CS-100. The devices emitted blue light with a peak emission at 450 nanometers, indicating that the EL emission originates from the triazine layer.

EXAMPLE VII

An organic EL device was prepared in accordance with Example VI except that 4,4'-bis-[2-(4,6-di-p-tolyl-1,3,5-triazinyl)]-1,1'-biphenyl was utilized in place of 4,4'-bis-[2-(4,6-diphenyl-1,3,5-triazinyl)]-1,1'-biphenyl. The light output from this organic EL device was 400 cd/m² when it was driven by a direct bias voltage of 8.0 volts. The EL color was blue with CIE color coordinates of X=0.145 and Y=0.087. The device emitted blue light with a peak emission at 448 nanometers, indicating that the EL emission originates from the triazine layer.

EXAMPLE VIII

An organic EL device was prepared in accordance with Example VI except that 4,4'-bis-[2-(4,6-di-m-tolyl-1,3,5-triazinyl)]-1,1'-biphenyl was selected in place of 4,4'-bis-[2-(4,6-diphenyl-1,3,5-triazinyl)]-1,1'-biphenyl. The light output from the resulting organic EL device was 150 cd/m² when it was driven by a direct bias voltage of 9.5 volts. The device emitted blue light with a peak emission at 440 nanometers, indicating that the EL emission originated from the triazine layer.

EXAMPLE IX

An organic EL device was prepared in accordance with Example VI except that 4,4'-bis-[2-(4,6-diphenyl-1,3,5-triazinyl)]-stilbene was selected in place of 4,4'-bis-[2-(4,6-diphenyl-1,3,5-triazinyl)]-1,1'-biphenyl. The light output from this organic EL device was 250 cd/m² when it was driven by a direct bias voltage of 8.5 volts. The EL color was blue with CIE color coordinates of X=0.159 and Y=0,161. The device emitted blue light with a peak emission at 453 nanometers, indicating that the EL emission originated from the triazine layer.

COMPARATIVE EXAMPLE I

A control organic EL device was fabricated in accordance with Example IX except that 4,4'-(hexafluoroisopropylidene)-bis-[4-phenoxyphenyl-4-(4,6-diphenyl-1,3,5-triazine)] of the following formula was selected as the electron transport layer in place of 4,4'-bis-[2-(4,6-diphenyl-1,3,5-triazinyl)]-1,1'-biphenyl.

(VI)

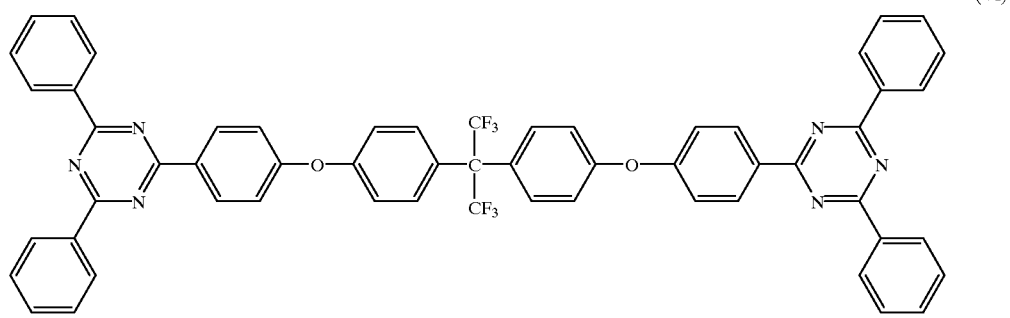

The light output from this organic EL device was not detectable when it was driven by a direct bias voltage of 8.5 volts. This Example indicates that a triazine compound without a group comprised of at least two fused or conjugate-linked aromatic rings was apparently not suitable as an electron transport or light emitting component.

EXAMPLE X

This Example illustrates the preparation of an organic EL device which further contains a light emitting layer.

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about 5×10⁻⁶ Torr, a 60 nanometers thick hole transport layer of N,N'-1-naphthyl-N,N'-diphenyl-1,1'-biphenyl-4,4'-diamine was deposited on the ITO glass substrate through simultaneous evaporation at a rate of 0.5 nanometer/second and rubrene was deposited at a rate of 0.02 nanometer/second from two independently controlled tantalum boats.

3. Onto the hole transport layer was deposited a 75 nanometer light emitting layer by the simultaneous evaporation of tris-(8-hydroxyquinolinato)aluminum at a rate of 0.5 nanometer/second and a fluorescent dye of rubrene at a rate of 0.02 nanometer/second from two independently controlled tantalum boats.

4. A 10 nanometer thick electron transport layer of 4,4'-bis-[2-(4,6-diphenyl-1,3,5-triazinyl)]-1,1'-biphenyl was then deposited by evaporation at a rate of 0.6 nanometer/second.

5. A 100 nanometer cathode of a magnesium silver alloy was deposited at a total deposition rate of 0.5 nanometer/second onto the electron transport layer by the simultaneous evaporation from two independently controlled tantalum boats containing Mg and Ag, respectively. A typical composition was 9:1 in atomic ratio of Mg to Ag. Finally, a 80 nanometer silver layer was overcoated on the Mg:Ag cathode for the primary purpose of protecting the reactive Mg from ambient moisture.

When driven by a direct bias voltage, the above EL device emitted a yellow light with a peak emission at 560 nanometers, indicating that the EL emission originated from the triazene layer. The device exhibited high luminance and satisfactory stability. Under a direct current density of 25 mA/cm$^2$, it provided a light intensity of about 1480 cd/m$^2$, and maintained about 65 percent of its initial luminance after continuous operation for 300 hours.

EXAMPLE XI

An EL device was fabricated in accordance with Example X except that 2,4,6-tris-(4-biphenylyl)-1,3,5-triazine as prepared in Example IV was selected as the electron transport material in place of 4,4'-bis-[2-(4,6-diphenyl-1,3,5-triazinyl)]-1,1'-biphenyl. The device exhibited high luminance and satisfactory stability. Under a direct current density of 25 mA/cm$^2$, it provided a light intensity of about 1,350 cd/m$^2$, and maintained about 80 percent of its initial luminance after continuous operation for 200 hours.

EXAMPLE XII

An EL device was fabricated in accordance with Example X except that 4,4'-bis-[2-(4,6-di-m-tolyl-1,3,5-triazinyl)]-1,1'-biphenyl was selected as the electron transport in place of 4,4'-bis-[2-(4,6-diphenyl-1,3,5-triazinyl)]-1,1'-biphenyl. This device exhibited high luminance and satisfactory stability; under a direct current density of 25 mA/cm$^2$, it provided a light intensity of about 1,450 cd/m$^2$, and maintained about 60 percent of its initial luminance after continuous operation for 300 hours.

EXAMPLE XIII

An EL device was fabricated in accordance with Example X except that 4,4'-bis-[2-(4,6-di-p-tolyl-1,3,5-triazinyl)]-1,'-biphenyl was selected as the electron transport in place of 4,4'-bis-[2-(4,6-diphenyl-1,3,5-triazinyl)]-1,1'-biphenyl. This device exhibited high luminance and satisfactory stability; under a direct current density of 25 mA/cm$^2$, it provided a light intensity of about 1,250 cd/m$^2$, and maintained 65 percent of its initial luminance after continuous operation for 200 hours.

EXAMPLE XIV

An EL device was fabricated in accordance with Example X except that 4,4'-bis-[2-(4,6-di-m-methoxyphenyl-1,3,5-triazinyl)]-1,1'-biphenyl was utilized as the electron transport in place of 4,4'-bis-[2-(4,6-diphenyl-1,3,5-triazinyl)]-1,1'-biphenyl. This device exhibited high luminance and excellent stability; under a direct current density of 25 mA/cm$^2$ it provided a light intensity of about 1,150 cd/m$^2$, and maintained about 50 percent of its initial luminance after continuous operation for 300 hours.

COMPARATIVE EXAMPLE II

A control organic EL device was fabricated in accordance with Example X except that 2,4,6-triphenyl-1,3,5-triazine illustrated by Formula (VI) as follows

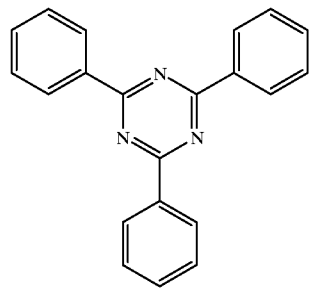

was utilized as the electron transport layer in place of 4,4,4'-bis-[2-(4,6-diphenyl-1,3,5-triazinyl)]-1,1'-biphenyl. This compound does not contain an aromatic group comprised of at least two conjugate-linked or fused aromatic rings.

This device exhibited lower luminance and poor stability; under a direct current density of 25 mA/cm$^2$, it provided a light intensity of about 900 cd/m$^2$, and only about 10 percent of its initial luminance was detected after continuous operation for 10 hours.

COMPARATIVE EXAMPLE III

A control organic EL device was fabricated in accordance with Example X except that 2,4,6-tri-2-pyridyl-1,3,5-triazine was utilized as the electron transport layer in place of 4,4'-bis-[2-(4,6-diphenyl-1,3,5-triazinyl)]-1,1'-biphenyl. This Comparative Example compound did not contain an aromatic group comprised of at least two conjugate-linked or fused aromatic rings.

This device exhibited poor stability; under a direct current density of 25 mA/cm$^2$, it provided a light intensity of about 1,350 cd/m$^2$, and less than 10 percent of its initial luminance was detected after continuous operation for 10 hours.

COMPARATIVE EXAMPLE IV

A control organic EL device was fabricated in accordance with Example X except that 2,4,6-triphenoxyl-1,3,5-triazine was utilized as the electron transport layer in place of 4,4'-bis-[2-(4,6-diphenyl-1,3,5-triazinyl)]-1,1'-biphenyl. This Comparative Example compound does not contain an aromatic group comprised of at least two conjugate-linked or fused aromatic rings.

This device exhibited low luminance and poor stability; under a direct current density of 25 mA/cm$^2$, it provided a light intensity of about 300 cd/m$^2$, and less than 30 percent of its initial luminance was detected after continuous operation for 10 hours.

EXAMPLE XV

This Example illustrated an organic EL device which utilizes aluminum as the cathode. The device was fabricated in the following manner:

1. A 500 Å indium tin oxide (ITO) anode coated glass substrate, the thickness of the glass substrate being about 1 millimeter, was cleaned with a commercial detergent, rinsed with deionized water and dried in a vacuum oven at 60° C. for 1 hour. Immediately before use, the glass was treated with UV ozone for 0.5 hour.

2. The ITO anode coated on the glass substrate was then placed in a vacuum deposition chamber. The deposition rate and layer thickness were controlled by an Inficon Model IC/5 controller. Under a pressure of about 5×10$^{-6}$ Torr, a 60 nanometers thick hole transport layer of N,N'-1-naphthyl-N,N'-diphenyl-1,1'-biphenyl-4,4'-diamine was deposited on the ITO glass substrate through simultaneous evaporation at a rate of 0.5 nanometer/second and evaporation of rubrene at a rate of 0.02 nanometer/second from two independently controlled tantalum boats.

3. Onto the hole transport layer was deposited a 75 nanometer light emitting layer by the simultaneous evaporation of tris-(8-hydroxyquinolinato)aluminum at a rate of 0.5 nanometer/second and a fluorescent dye of rubrene at a rate of 0.02 nanometer/second from two independently controlled tantalum boats.

4. A 10 nanometer thick electron transport layer was then deposited by evaporation of 4,4'-bis-[2-(4,6-diphenyl-1,3,5-triazinyl)]-1,1'-biphenyl at a rate of 0.6 nanometer/second.

5. A 100 nanometer cathode of aluminum was deposited at a total deposition rate of 0.5 nanometer/second onto the electron transport layer by evaporation from a tantalum boat containing aluminum.

When driven by a direct bias voltage, the resulting EL device emitted a yellow light with a peak emission at 560 nanometers. The device exhibited high luminance and satisfactory stability; under a direct current density of 25 mA/cm$^2$, it provided a light intensity of about 1,020 cd/m$^2$ with an initial voltage at 9.7 volts and maintained about 75 percent of its initial luminance after continuous operation for 500 hours.

COMPARATIVE EXAMPLE V

A control organic EL device was fabricated in accordance with Example XV except that tris-(8-hydroxyquinolinato)aluminum was selected as the electron transport layer in place of 4,4,4'-bis-[2-(4,6-diphenyl-1,3,5-triazinyl)]-1,1'-biphenyl.

This device exhibited lower luminance and poor stability; under a direct current density of 25 mA/cm$^2$ it provided a light intensity of about 800 cd/m$^2$ with an initial voltage at 10.5 volts, and less than 25 percent of its initial luminance remained after continuous operation for 10 hours.

Other modifications of the present invention will or may occur to those of ordinary skill in the art subsequent to a review of the present application. These modifications and equivalents thereof are intended to be included within the scope of the present invention.

What is claimed is:
1. The triazine

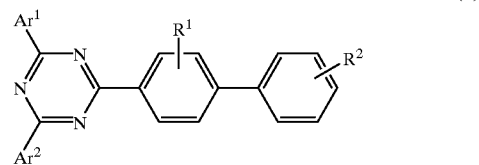

(II)

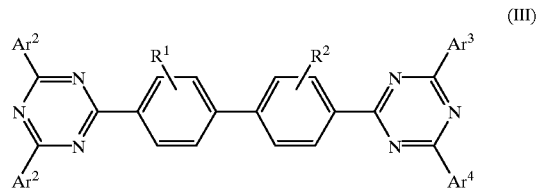

(III)

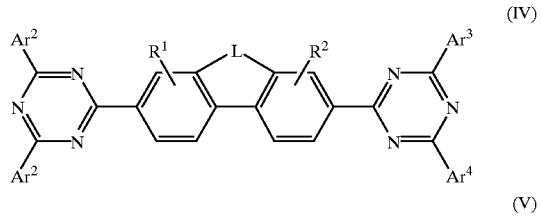

(IV)

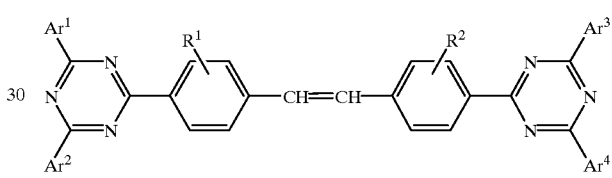

(V)

wherein Ar$^1$, Ar$^2$, Ar$^3$, and Ar$^4$ are each independently an aryl; R$^1$ and R$^2$ are substituents selected from the group consisting of hydrogen, an alkyl, an aryl, an alkoxy, a halogen atom, and a cyano; R$^3$ and R$^4$ are each a group L selected from the group consisting of —C(R'R")—, alkylene, an oxygen atom, a sulfur atom, and —Si(R'R")—, wherein R' and R" are selected from the group consisting of hydrogen, alkyl, alkoxy, and aryl.

2. A triazine in accordance with claim 1 wherein Ar$^1$, Ar$^2$, Ar$^3$, and Ar$^4$ are selected from the group consisting of a phenyl, a biphenylyl, a naphthyl, and a stilbenyl; and wherein said aryl group contains a substituent selected from the group consisting of hydrogen, an alkyl group with from 1 to about 6 carbon atoms, an alkoxy group with from 1 to about 6 carbon atoms, a halogen atom, and a cyano group.

3. A triazine in accordance with claim 1 wherein said aryl is selected from the group consisting of a phenyl, a tolyl, a methoxyphenyl, a butylphenyl, a naphthyl, and a biphenylyl; and wherein R$^1$ and R$^2$ are hydrogen or methyl.

4. A triazine in accordance with claim 1 wherein L is —C(R'R")—, wherein R' and R" is a hydrogen atom, an alkyl group containing from 1 to about 10 carbon atoms, or an alkoxyl group containing from 1 to about 10 carbon atoms.

5. A triazine selected from the group consisting of 2,4,6-tris(4-biphenylyl)-1,3,5-triazine, 2,4,6-tris[4-(4'-methylbiphenylyl)]-1,3,5-triazine, 2,4,6-tris[4-(4'-tert-butylbiphenylyl)-1, 3,5-triazine, 2,4,6-tris[4-(4'-methoxybiphenylyl)]-1,3,5-triazine, 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-

(4,6-di-m-methoxyphenyl-1,3,5-triazinyl)]-1,1'-biphenyl, 4,4'-bis-[2-(4-0-naphthyl-6-phenyl-1,3,5-triazinyl)]-1,1'-biphenyl, 2,7-bis-[2-(4,6-di-phenyl-1,3,5-triazinyl)]fluorene, 2,7-bis-[2-(4,6-di-phenyl-1,3,5-triazinyl)]-9,9-dimethylfluorene, 4,4'-bis-[2-(4,6-di-phenyl-1,3,5-triazinyl)]-stilbene, and 4,4'-bis-(2-(4-phenyl-6-m-tolyl-1,3,5-triazinyl)]-stilbene.

6. A triazine selected from the group consisting of 2,4,6-tris(4-biphenylyl)-1,3,5-triazine, 4,4'-bis-[2-(4,6-diphenyl-1,3,5-triazinyl)]-1,1'-biphenyl, 4,4'-bis-[2-(4,6-di-p-tolyl-1,3,5-triazinyl)]-1,1'-biphenyl, 4,4'-bis-[2-(4,6-di-m-tolyl-1,3,5-triazinyl)]-1,1'-biphenyl, 4,4'-bis-[2-(4,6-di-p-methoxyphenyl-1,3,5-triazinyl)]-1,1'-biphenyl, 4,4'-bis-[2-(4,6-di-p-tert-butylphenyl-1,3,5-triazinyl)]-1,1'-biphenyl, and 4,4'-bis-[2-(4,6-di-phenyl-1,3,5-triazinyl)]-stilbene.

7. A triazine in accordance with claim 1 wherein $Ar^1$, $Ar^2$, $Ar^3$ and $Ar^4$ are phenyl.

8. A triazine in accordance with claim 1 wherein $Ar^1$, $Ar^2$, $Ar^3$ and $Ar^4$ are naphthyl.

9. A triazine in accordance with claim 1 wherein $Ar^1$, $Ar^2$, $Ar^3$ and $Ar^4$ are aryl with from about 6 to about 30 carbon atoms.

10. A triazine in accordance with claim 1 wherein $R^1$ and $R^2$ are aryl.

11. A triazine in accordance with claim 1 wherein $R^3$ and $R^4$ are alkylene with from about 2 to about 24 carbon atoms.

12. A triazine in accordance with claim 1 wherein R' and R" are alkyl with about 1 to about 25 carbon atoms.

13. A triazine in accordance with claim 1 wherein R' and R" are alkyl with about 1 to about 6 carbon atoms.

14. A triazine in accordance with claim 1 wherein R' and R" are alkoxy with about 1 to about 25 carbon atoms.

15. A triazine in accordance with claim 1 wherein R' and R" are alkoxy with about 1 to about 6 carbon atoms.

16. A triazine in accordance with claim 1 wherein $R^3$ is oxygen.

17. A triazine in accordance with claim 1 wherein $R^4$ is oxygen.

18. A triazine of the formula

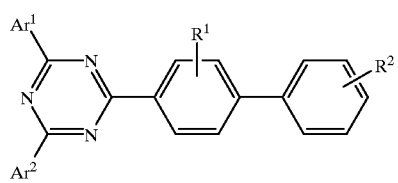

wherein $Ar^1$, and $Ar^2$ are each independently an aryl; and $R^1$ and $R^2$ are selected from the group consisting of hydrogen, an alkyl, an aryl, an alkoxy, a halogen atom, and a cyano.

19. A triazine of the formula

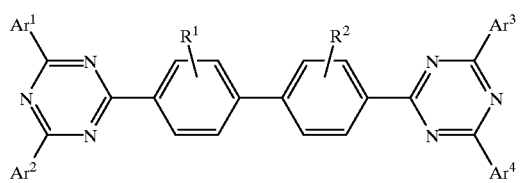

wherein $Ar^1$, $Ar^2$, $Ar^3$, and $Ar^4$ are each independently an aryl; $R^1$ and $R^2$ are selected from the group consisting of hydrogen, an alkyl, an aryl, an alkoxy, a halogen atom, and a cyano.

20. A triazine of the formula

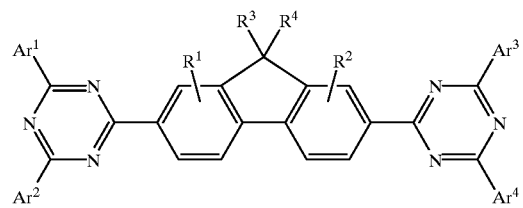

wherein $Ar^1$, $Ar^2$, $Ar^3$, and $Ar^4$ are each independently an aryl; $R^1$ and $R^2$ are selected from the group consisting of hydrogen, an alkyl, an aryl, an alkoxy, a halogen atom, and a cyano; $R^3$ and $R^4$ are each selected from the group consisting of —C(R'R")—, alkylene, an oxygen atom, a sulfur atom, and —Si(R'R")—, wherein R' and R" are selected from the group consisting of hydrogen, alkyl, alkoxy, and aryl.

21. A triazine of the formula

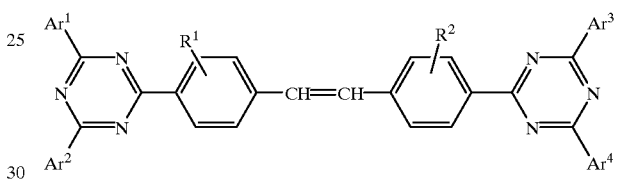

wherein $Ar^1$, $Ar^2$, $Ar^3$, and $Ar^4$ are each independently an aryl; $R^1$ and $R^2$ are selected from the group consisting of hydrogen, an alkyl, an aryl, an alkoxy, a halogen atom, and a cyano.

22. An electroluminescent device containing as the electron transport a triazine of claim 1.

23. An electroluminescent device containing as the electron transport a triazine of claim 18.

24. An electroluminescent device containing as the electron transport a triazine of claim 19.

25. An electroluminescent device containing as the electron transport a triazine of claim 20.

26. An electroluminescent device containing as the electron transport a triazine of claim 21.

27. A triazine of the formulas (II)

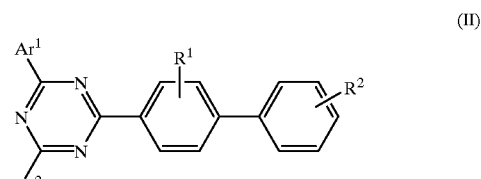

(III)

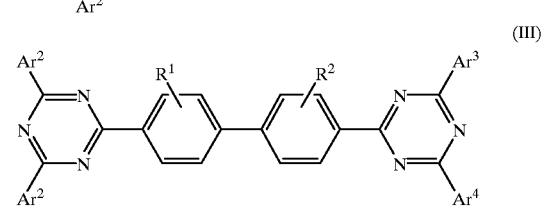

-continued

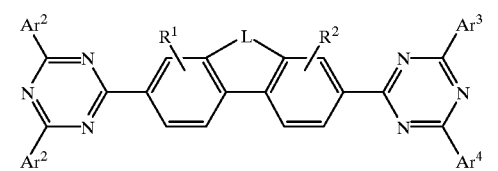
(IV)

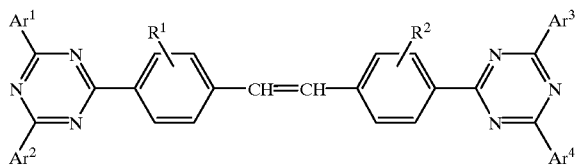
(V)

wherein $Ar^1$, $Ar^2$, $Ar^3$, and $Ar^4$ are each independently aromatic or aliphatic; $R^1$ and $R^2$ are selected from the group consisting of hydrogen, an alkyl, an aryl, an alkoxy, a halogen atom, and a cyano; $R^3$ and $R^4$ are each selected from the group consisting of —C(R'R'')—, alkylene, an oxygen atom, a sulfur atom, and —Si(R'R'')—, wherein R' and R'' are selected from the group consisting of hydrogen, alkyl, alkoxy, and aryl, and $Ar^1$, $Ar^2$, $Ar^3$, and $Ar^4$ are aryl.

28. A triazine in accordance with claim 27 wherein $Ar^1$, $Ar^2$, $Ar^3$, and $Ar^4$ are selected from the group consisting of a phenyl, a biphenylyl, a naphthyl, and a stilbenyl; and wherein said aryl group contains a substituent selected from the group consisting of hydrogen, an alkyl group with from 1 to about 6 carbon atoms, an alkoxy group with from 1 to about 6 carbon atoms, a halogen atom, and a cyano group.

29. A triazine in accordance with claim 27 wherein alkyl contains from 1 to about 25 carbon atoms, and alkoxy contains from 1 to about 25 carbon atoms, and wherein said $R^1$ and $R^2$ are alkyl, or alkoxy.

\* \* \* \* \*